(12) United States Patent
Rocchi et al.

(10) Patent No.: US 9,567,310 B2
(45) Date of Patent: Feb. 14, 2017

(54) BENZENE SULFONAMIDE THIAZOLE COMPOUNDS

(71) Applicants: INSERM (INSTITUT NATIONAL DE LA SANTE ET DE LA RECHERCHE MEDICALE), Paris (FR); UNIVERSITE NICE SOPHIA ANTIPOLIS, Nice (FR); CENTRE NATIONAL DE LA RECHERCHE SCIENTIFIQUE (CNRS), Paris (FR)

(72) Inventors: Stephane Rocchi, Nice (FR); Robert Ballotti, Nice (FR); Rachid Benhida, Nice (FR); Michael Cerezo, Nice (FR); Maria Duca, Nice (FR); Jean-Patrick Joly, Nice (FR)

(73) Assignees: INSERM (INSTITUT NATIONAL DE LA SANTE ET DE LA RECHERCHE MEDICALE), Paris (FR); UNIVERSITE NICE SOPHIA ANTIPOLIS, Paris (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 0 days.

(21) Appl. No.: 14/441,717

(22) PCT Filed: Nov. 8, 2013

(86) PCT No.: PCT/EP2013/073439
§ 371 (c)(1),
(2) Date: May 8, 2015

(87) PCT Pub. No.: WO2014/072486
PCT Pub. Date: May 15, 2014

(65) Prior Publication Data
US 2015/0284347 A1 Oct. 8, 2015

(30) Foreign Application Priority Data

Nov. 9, 2012 (EP) .................................... 12306391

(51) Int. Cl.
*C07D 277/42* (2006.01)
*C07D 277/46* (2006.01)
(Continued)

(52) U.S. Cl.
CPC ........... *C07D 277/42* (2013.01); *C07D 277/46* (2013.01)

(58) Field of Classification Search
CPC ..... C07D 277/42; C07D 277/46; A61P 35/00; A61K 31/426
(Continued)

(56) References Cited

U.S. PATENT DOCUMENTS

2009/0298815 A1* 12/2009 Adams ................ C07D 413/04
514/227.8
2011/0319392 A1* 12/2011 Adjabeng ............ C07D 417/04
514/218

FOREIGN PATENT DOCUMENTS

WO 2006/051270 A1 5/2006
WO 2007/129044 A1 11/2007
(Continued)

OTHER PUBLICATIONS

Chemical Abstracts STN Database Record for RN 476338-88-2 entered on Dec. 16, 2002.*
(Continued)

*Primary Examiner* — Noble Jarrell
*Assistant Examiner* — Daniel Carcanague
(74) *Attorney, Agent, or Firm* — Whitham, Curtis & Cook, P.C.

(57) ABSTRACT

The present invention relates to compound of general formula (1) wherein $R_1$ represents $C_6$-$C_{10}$ aryl comprising one
(Continued)

Figure 1:
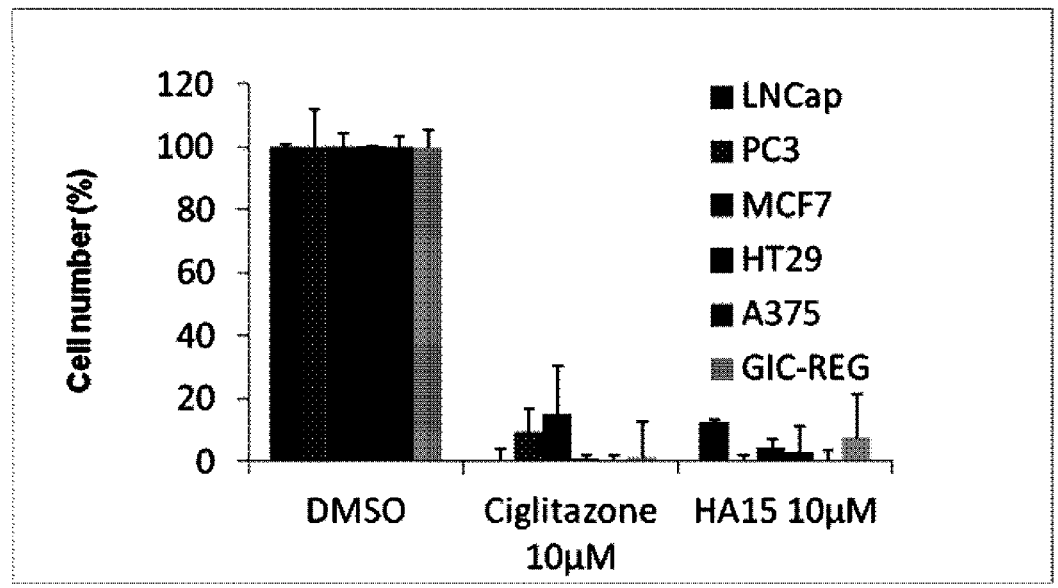

or two fused rings, wherein from 2 to 5 carbon atoms may be replaced with a heteroatom selected from O, S and $NR_6$, and eventually substituted with from 5 to 11 substituents selected from $R_6$, halo, CN, $NO_2$, $CF_3$, $OCF_3$, $COOR_6$, $OCOR_6$, $SO_2NR_6R_7$, $CONR_6R_7$, $NR_6R_7$, $NR_6COR_7$, $(CH_2)_p$—$NR_6R_7$, $(CH_2)_p$—$OR_6$ and $(CH_2)_pSR_6$, as well as, if appropriate, their pharmaceutically acceptable salts and/or isomers, tautomers, solvates or isotopic variations thereof. The compounds are useful for the treatment of cancers.

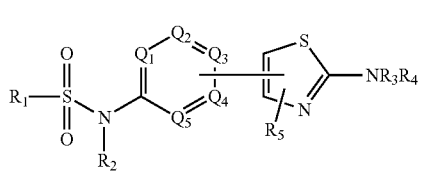

(1)

3 Claims, 3 Drawing Sheets

(51) Int. Cl.
*A61P 35/00* (2006.01)
*A61K 31/426* (2006.01)

(58) Field of Classification Search
USPC .................................................. 546/268.1
See application file for complete search history.

(56) References Cited

FOREIGN PATENT DOCUMENTS

| WO | WO2009146013 | * 12/2009 |
|----|--------------|-----------|
| WO | WO2012113774 | * 8/2012 |
| WO | WO2013052845 | * 4/2013 |

OTHER PUBLICATIONS

Korgaokar J. Inst. Chem. (India) 2001, 73, 209-211.*
Korgaokar et al., "Studies on 2-aminothiazoles: 2-aroylamino-4-[m-(p-chlorobenzenesulfonam ido)phenyl] thiazoles", Journal of the Institution of Chemists, 2001, pp. 209-211, vol. 73, No. 6.
Giovanni et al., "Overwhelming response to Dabrafenib in a patient with double BRAF mutation (V600; V600M) metastatic malignant melanoma", Journal of Hematology & Oncology, Oct. 2, 2012, p. 60, vol. 5, No. 1.

* cited by examiner

BENZENE SULFONAMIDE THIAZOLE COMPOUNDS

FIELD OF THE INVENTION

The invention relates to new benzene sulfonamide thiazole compounds active for the treatment of cancers.

BACKGROUND OF THE INVENTION

Cutaneous melanoma deriving from the transformation of melanocytes is one of the most lethal cancers among young adults. Its incidence has increased at a dramatic rate during the last decades. Melanoma has a high capability of invasion and rapid metastasis to other organs. The prognosis of metastatic melanoma is extremely pejorative, as the various protocols of chemotherapy or immunotherapy have not shown real survival benefit. Indeed, at the ganglionic metastatic stage, the forecast deteriorates considerably with a survival rate after 5 years of 50%. At the stage of visceral metastases, the forecast is catastrophic with a median of survival of 6 months. Therefore, the melanoma, which represents only 5% of the cutaneous cancers, represents 80% of the deaths associated to this type of cancer. With an incidence, which doubles every ten years (10000 new cases in France in 2007), the melanoma constitutes a real problem of public health. Finally, even if recently encouraging results were obtained with vemurafenib and dabrafenib, two inhibitors of the B-Raf pathway, the responses remain transitory. Indeed, vemurafenib and dabrafenib target only melanomas mutated on B-Raf (approximately 50% of the metastatic melanomas). Unfortunately, after a short period of regression, the melanoma acquires in all cases, a resistance against the drug and the metastases develop again, increasing only about 2 months the life expectancy of the patient. The identification of these mechanisms of resistance is now the subject matter of numerous works but no study managed to clearly identify the mechanisms involved.

Recently, the anti-CTLA4 antibody ipilimumab able to reactivate the immune response of the patient was developed for the treatment of melanoma. However, this approach provides an objective response in only 10 to 15% of the patients.

The identification of new candidate molecules is thus a major aim for the development of specific biotherapies.

The inventors of the instant invention were initially interested in a family of molecules used in the treatment of the type 2 diabetes, the thiazolidinediones (TZD). The effect of PPAR gamma on glucose metabolism is mediated by activation of nuclear receptor, PPAR gamma.

The inventors have previously shown that some TZD led to a massive death of the cells in in vitro as well as in in vivo models of melanoma independently of PPAR gamma activation.

Taken together, the inventors synthesized and identified a family of compounds derived from TZD that led to a loss of viability of the melanoma cells.

The compounds of the inventions thus show a high potency in vitro as well as in vivo models of melanoma. Interestingly, although the compounds of the invention present structure similarities with dabrafenib, their signaling pathways and their mechanisms of action are totally different from those of dabrafenib.

In addition, it appears that the compounds of the invention are also efficient on several other cancers namely prostate, breast and colon indicating that these molecules may be active in all type of cancers.

SUMMARY OF THE INVENTION

The invention relates to benzene sulfonamide thiazole compounds of general formula:

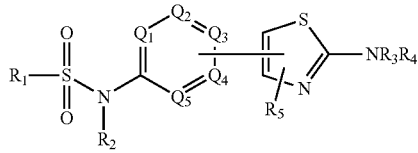

in which $Q_1$, $Q_2$, $Q_3$, $Q_4$, $Q_5$, $R_1$ to $R_5$ and n have the meanings indicated below, and to processes for the preparation of, compositions containing and the uses of such derivatives.

DETAILED DESCRIPTION OF THE INVENTION

The invention relates to compounds of general formula (1):

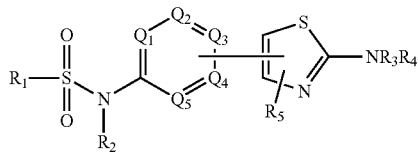

wherein $Q_1$ to $Q_5$ identical or different represent $CR_6$, $R_1$ represents $C_6$-$C_{10}$ aryl comprising one or two fused rings, wherein from 2 to 5 carbon atoms may be replaced with a heteroatom selected from O, S, N and $NR_6$, and eventually substituted with from 5 to 11 substituents selected from $R_6$, halo, CN, $NO_2$, $CF_3$, $OCF_3$, $COOR_6$, $OCOR_6$, $SO_2NR_6R_7$, $CONR_6R_7$, $NR_6R_7$, $NR_6COR_7$, $(CH_2)_p$—$NR_6R_7$, $(CH_2)_p$—$OR_6$ and $(CH_2)_p SR_6$, $R_2$ is $SO_2R_1$ or $R_6$ $R_3$ and $R_4$ identical or different are selected from $COR_8$ and $R_6$ $R_5$ represents $R_6$, aryl, $OR_6$, $SR_6$, halo, CN, $NO_2$, $CF_3$, $OCF_3$, $COOR_6$, $SO_2NR_6R_7$, $CONR_6R_7$, $NR_6R_7$ and $NHCOR_6$, $R_6$ and $R_7$ identical or different represent H or alkyl $R_8$ is selected from H, alkyl, cycloalkyl, aryl, alkylaryl, wherein aryl may be substituted with from one to four $R_5$ substituents identical or different, or $R_8$ represents $(CH_2)_q NR_6R_7$, p represents an integer from 0 to 6, q represents an integer from 0 to 6, wherein the thiazolyl group is linked to the 6 member group in meta or para position with respect to the sulfonamide group and wherein the thiazolyl group is linked to the 6-member group in position α or β with respect to the S atom, with the exclusion of the following compounds:

N-[4-[3-[[(4-chlorophenyl)sulfonyl]amino]phenyl]-2-thiazolyl]-2-hydroxy-benzamide, 2-(acetyloxy)-N-[4-[3-[[(4-chlorophenyl)sulfonyl]amino] phenyl]-2-thiazolyl]-benzamide, 3-chloro-N-[4-[3-[[(4-chlorophenyl)sulfonyl]amino]phenyl]-2-thiazolyl]-benzamide, N-[4-[3-[[(4-chlorophenyl)sulfonyl]amino]phenyl]-2-thiazolyl]-1-hydroxy-2-naphtalenecarboxamide,
N-[4-[3-[[(4-chlorophenyl)sulfonyl]amino]phenyl]-2-thiazolyl]-3-hydroxy-2-naphtalenecarboxamide,
N-[4-[3-[[(4-chlorophenyl)sulfonyl]amino]phenyl]-2-thiazolyl]-2-methoxy-benzamide,
N-[3-(2-amino-4-thiazolyl)phenyl]-4-chloro-benzenesulfonamide,
N-[4-[3-[[(4-chlorophenyl)sulfonyl]amino]phenyl]-2-thiazolyl]-benzamide,
2-chloro-N-[4-[3-[[(4-chlorophenyl)sulfonyl]amino]phenyl]-2-thiazolyl]-benzamide,
4-chloro-N-[4-[3-[[(4-chlorophenyl)sulfonyl]amino]phenyl]-2-thiazolyl]-benzamide,
N-[4-[3-[[(4-chlorophenyl)sulfonyl]amino]phenyl]-2-thiazolyl]-3,4-dimethoxy benzamide,
N-[4-[3-[[(4-chlorophenyl)sulfonyl]amino]phenyl]-2-thiazolyl]-3-methoxy benzamide,
N-[4-[3-[[(4-chlorophenyl)sulfonyl]amino]phenyl]-2-thiazolyl]-4-methoxy benzamide,
N-[4-[3-[[(4-chlorophenyl)sulfonyl]amino]phenyl]-2-thiazolyl]-3-methyl-benzamide,
N-[4-[3-[[(4-chlorophenyl)sulfonyl]amino]phenyl]-2-thiazolyl]-4-methyl-benzamide,
N-[4-[3-[[(4-chlorophenyl)sulfonyl]amino]phenyl]-2-thiazolyl]-4-nitro-benzamide,
N-[4-[3-[[(4-chlorophenyl)sulfonyl]amino]phenyl]-2-thiazolyl]-4-methyl-benzamide,
or, if appropriate, their pharmaceutically acceptable salts and/or isomers, tautomers, solvates or isotopic variations thereof.

A preferred group is comprised of compounds of general formula (2)

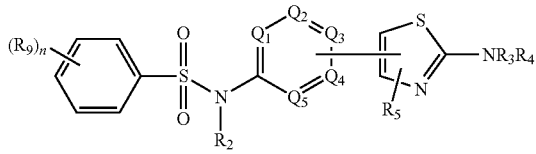

wherein $Q_1$ to $Q_5$, $R_2$, $R_3$ and $R_4$ are as defined above and $R_9$ represents $R_6$, halo, CN, $NO_2$, $CF_3$, $OCF_3$, $COOR_6$, $OCOR_6$, $SO_2NR_6R_7$, $CONR_6R_7$, $NR_6R_7$, $NR_6COR_7$, $(CH_2)_p$—$NR_6R_7$, $(CH_2)_p$—$OR_6$ and $(CH_2)_p SR_6$,
wherein $R_6$ and p are as defined above and n represents 1, 2, 3 or 4.

Another preferred group is comprised of compounds of general formula (3)

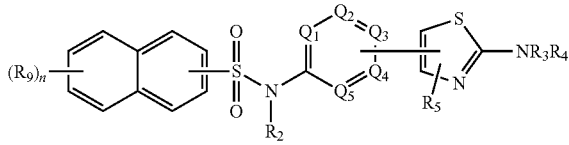

wherein $Q_1$ to $Q_5$, $R_2$, $R_3$ and $R_4$ are as defined above and $R_9$ represents $R_6$, halo, CN, $NO_2$, $CF_3$, $OCF_3$, $COOR_6$, $OCOR_6$, $SO_2NR_6R_7$, $CONR_6R_7$, $NR_6R_7$, $NR_6COR_7$, $(CH_2)_p$—$NR_6R_7$, $(CH_2)_p$—$OR_6$ and $(CH_2)_p SR_6$,
wherein $R_6$ and p are as defined above and n represents 1, 2, 3 or 4 and the naphtyl group is attached to the sulfur atom in position 1, 2 or 3 with respect to the quaternary carbons.

In the above general formulae (1), (2) and (3),
$R_2$ preferably represents H, or $SO_2R_1$, wherein $R_2$ is phenyl or naphtyl group optionally substituted with from 1 to 4, preferably one or two substituents selected from $R_6$, halo, CN, $NO_2$, $CF_3$, $OCF_3$, $COOR_6$, $OCOR_6$, $SO_2NR_6R_7$, $CONR_6R_7$, $NR_6R_7$, $NR_6COR_7$, $(CH_2)_p$—$NR_6R_7$, $(CH_2)_p$—$OR_6$ and $(CH_2)_p SR_6$; preferred substituents are $R_6$, halo, $CF_3$, $NR_6R_7$, wherein $R_6$ and $R_7$ represent H or methyl.

Preferably $R_3$ represents H and $R_4$ represents H, alkyl, CO-alkyl, aryl, wherein aryl comprises one or more substituents selected from $R_6$, halo, CN, $NO_2$, $CF_3$, $OCF_3$, $COOR_6$, $OCOR_6$, $SO_2NR_6R_7$, $CONR_6R_7$, $NR_6R_7$, $NR_6COR_7$, $(CH_2)_p$—$NR_6R_7$, $(CH_2)_p$—$OR_6$ and $(CH_2)_p SR_6$, wherein $R_6$, $R_7$ and p are as defined above.

$R_6$ is preferably H or alkyl $R_9$ is preferably $R_6$, halo, CN, $NO_2$, $CF_3$, $OCF_3$, $COOR_6$, $OCOR_6$, $SO_2NR_6R_7$, $CONR_6R_7$, $NR_6R_7$, $NR_6COR_7$, $(CH_2)_p$—$NR_6R_7$, $(CH_2)_p$—$OR_6$ and $(CH_2)_p SR_6$, The thiazolyl group is preferably in the meta position with respect to the sulfonamide group The thiazolyl group is also preferably linked to the 6 member aromatic ring in the β-position with respect to the sulfur atom.

In the above general formulae (1) to (3), alkyl denotes a straight-chain or branched group containing 1, 2, 3, 4 or 5 carbon atoms. This also applies if they carry substituents or occur as substituents of other radicals, for example in O-alkyl radicals, S-alkyl radicals etc. Examples of suitable alkyl radicals are methyl, ethyl, n-propyl, isopropyl, n-butyl, isobutyl, sec-butyl, tert-butyl, etc.

Cycloalkyl comprises 3 to 7 carbon atoms and f include cyclopropyl, cyclobutyl, cyclopentyl, cyclohexyl and cycloheptyl, Aryl denotes an aromatic carbon ring comprising from 6 to 10 carbon atoms.

Finally, halo denotes a halogen atom selected from the group consisting of fluoro, chloro, bromo and iodo in particular fluoro or chloro.

In the following, the free bond on the phenyl group such as in the structure below means that the phenyl can be substituted in the meta or para position.

Preferred compounds according to the invention are the following:
N-(4-(3-(5-(dimethylamino)naphthalene-1-sulfonamido)phenyl)thiazol-2-yl)acetamide
5-(dimethylamino)-N-(3-(2-(methylamino)thiazol-4-yl)phenyl)naphthalene-1-sulfonamide
N-(4-(3-(5-(dimethylamino)naphthalene-1-sulfonamido)phenyl)thiazol-2-yl)-4 methylbenzamide
N-(3-(2-aminothiazol-4-yl)phenyl)-5-(dimethylamino)naphthalene-1-sulfonamide
N-(4-(3-(5-(dimethylamino)naphthalene-1-sulfonamido)phenyl)thiazol-2-yl)benzamide
N-(4-(3-(5-(dimethylamino)naphthalene-1-sulfonamido)phenyl)thiazol-2-yl)pivalamide
2-fluoro-N-(3-(2-(methylamino)thiazol-4-yl)phenyl)benzenesulfonamide
N-(4-(4-(naphthalene-2-sulfonamido)phenyl)thiazol-2-yl)acetamide
N-(4-(4-(5-(dimethylamino)naphthalene-1-sulfonamido)phenyl)thiazol-2-yl)acetamide
N-(4-(4-(2-fluorophenylsulfonamido)phenyl)thiazol-2-yl)acetamide
N-(4-(4-(2,4-difluorophenylsulfonamido)phenyl)thiazol-2-yl)acetamide N-(4-(4-(3-(trifluoromethyl)phenylsulfonamido)phenyl)thiazol-2-yl)acetamide N-(4-(3-(3-(trifluoromethyl)phenylsulfonamido)phenyl)thiazol-2-yl)acetamide N-(4-(3-(3-(trifluoromethyl)phenylsulfonamido)phenyl)thiazol-2-yl)acetamide N-(4-(4-(4-(trifluoromethyl)phenylsulfonamido)phenyl)thiazol-2-yl)acetamide N-(4-(3-(4-methylphenylsulfonamido)phenyl)thiazol-2-yl)acetamide N-(4-(3-(2-nitrophenylsulfonamido)phenyl)thiazol-2-yl)acetamide N-(4-(3-(3-nitrophenylsulfonamido)phenyl)thiazol-2-yl)acetamide N-(4-(3-(phenylsulfonamido)phenyl)thiazol-2-yl)acetamide N-(4-(3-(methylsulfonamido)phenyl)thiazol-2-yl)acetamide N-(4-(4-(4-methylphenylsulfonamido)phenyl)thiazol-2-yl)acetamide N-(4-(3-(5-(dimethylamino)naphthalene-1-sulfonamido)phenyl)thiazol-2-yl)-6-amino-hexanamide The compounds of the formula (1) may be prepared using conventional procedures such as by the following illustrative methods (schemes 1-2) in which the various substituents are as previously defined for the compounds of the formula (1) unless otherwise stated.

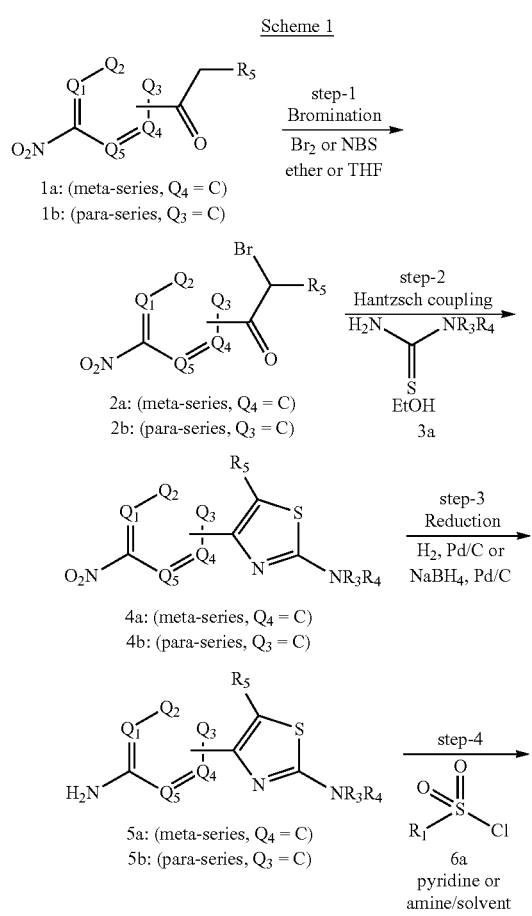

Scheme 1

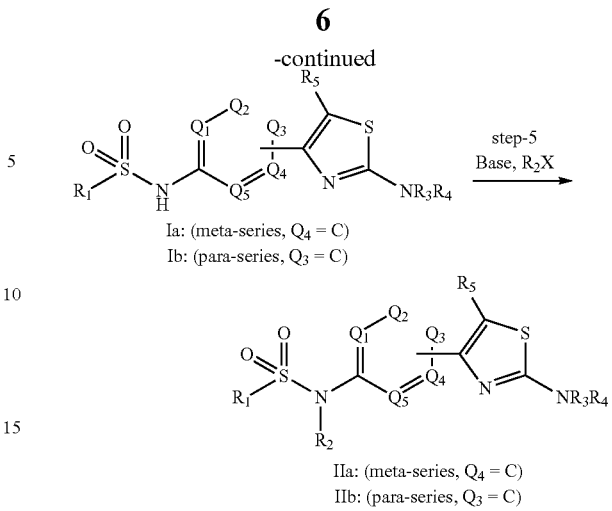

The procedure for preparing the compounds of the invention according to scheme 1 comprises the following steps:

Step 1 to prepare compound of formula 2a and 2b: 2a and 2b may be prepared by bromination of compounds of formula 1a or 1b with a suitable brominating agent $Br_2$ or N-bromosuccinimide (NBS) in solvents such as ether ($Et_2O$), THF or MeTHF, preferably in the presence of Lewis acid such as $AlCl_3$ (D. Guianvarch, R. Benhida, J-L. Fourrey, R. Maurisse, J-S. Sun. J. Chem. Soc. Chem. Comm. 2001, 1814-1815).

Step 2 to prepare compound of formula 4a and 4b: this step consists of condensing compound 2a or 2b with thiourea of formula 3a in suitable solvents that include but not restricted to EtOH, iPrOH, ethyl acetate, $CH_2Cl_2$, DMF. The reaction may be carried out at a temperature of about 25° C. to 100° C., preferably at 60-80° C. with or without acid or base catalyst depending on the reactivity of the starting material.

Step 3 to prepare compounds of formula 5a and 5b: the reduction may be carried out with a source of $H_2$ in the presence of metal catalyst which include but not limited to palladium derivatives on carbon, platinum derivatives on carbon or Raney nickel on carbon or other source of $H_2$ such as $NaBH_4$/Pd/C, metal under acidic conditions (iron, tin chloride, titanium chloride, Zinc in HCl or AcOH). The reaction could be realized in inert solvents that include but are not restricted to EtOH, MeOH, THF, dioxane, AcOH, ethylacetate, at either atmospheric or elevated pressure.

Step 4 to prepare compounds of formula Ia and Ib: the reaction is typically carried out by reacting compounds of formula 5a or 5b with sulfone chloride of formula 6a in an appropriate solvent such as $CH_2Cl_2$, AcOEt, DMF, DMSO, ether, THF, MeTHF, dioxane, acetonitrile in the presence of amine such as triethylamine, diisopropylethylamine, pyridine and substituted pyridines (for example DMAP). The reaction may be also carried out in pyridine as solvent.

Step 5 to prepare compounds of formula IIa and IIb: the reaction is typically carried out by reacting compounds of formula Ia or Ib with alkylating reagents $R_2X$ (X=halogen, preferably I, Br and Cl) in the presence of base which include but not limited to $K_2CO_3$, $Cs_2CO_3$, NaH, LDA, $Et_3N$, pyridine or substituted pyridines, in an appropriate solvent such as $CH_2Cl_2$, AcOEt, DMF, DMSO, THF, MeTHF, dioxane, acetonitrile.

Scheme 2

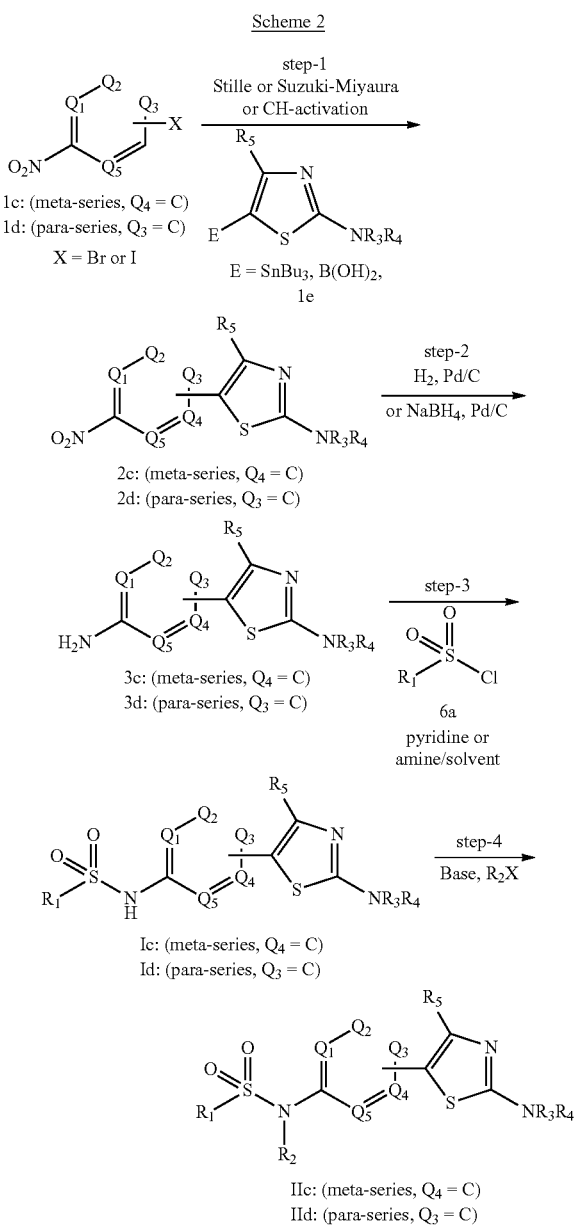

The procedure for preparing the compounds of the invention (compounds Ic and IIc, Id and IId) according to scheme 2 comprises the following steps:

Step 1 to prepare compound of formula 2c and 2d: the carbon-carbon formation may be achieved using techniques conventional in the art. In a typical reaction, compound of formula 1c and 1d (X=leaving group in palladium reactions, preferably Br or I) may be reacted with boron derivatives (Suzuki-Miyaura coupling, Palladium-Catalyzed Cross-Coupling Reactions of Organoboron Compounds N. Miyaura, A. Suzuki Chem. Rev., 1995, 95 (7), pp 2457-2483), tin derivatives (Stille coupling, J. K. Stille, Angew. Chem. Int. Ed. Engl. 1986, 25, 508-524, D. Guianvarc'h, J-L Fourrey, J-S. Sun, R. Maurisse, R. Benhida. Bioorg. Med. Chem. 2003, 11, 2751-2759) or by a direct C—H activation (J. Yamaguchi, A. D. Yamaguchi, K. Itami Angew. Chem. Int. Ed. 2012, 51, 8960-9009) in an appropriate solvent for example as DMF, DMSO, THF, MeTHF, dioxane, acetonitrile, in the presence of palladium catalyst for example $Pd(PPh_3)_4$, $Pd(PPh_3)_2Cl_2$, palladium dibenzylideneacetone at a temperature of 20 to 140° C., preferably, 25-70° C. Depending on the nature of starting materials, this reaction requires some time other additives such as base (carbonate, amine) and/or ligands (phosphines) and/or copper source for example CuI or other conventional additives in the art.

Steps 2, 3 and 4 in scheme 1 are similar to those described above in scheme 1, e.g., step 3, 4 and 5, respectively (reduction, sulfonylation and alkylation).

Pharmaceutically acceptable salts of the compounds of formula (1) include the acid addition and base salts thereof. Suitable acid addition salts are formed from acids, which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate and xinafoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts.

For a review on suitable salts, see "Handbook of Pharmaceutical Salts: Properties, Selection, and Use" by Stahl and Wermuth (Wiley-VCH, Weinheim, Germany, 2002). Pharmaceutically acceptable salts of compounds of formula (1) may be prepared by one or more of three methods:
 (i) by reacting the compound of formula (1) with the desired acid or base;
 (ii) by removing an acid- or base-labile protecting group from a suitable precursor of the compound of formula (1) or by ring-opening a suitable cyclic precursor, for example, a lactone or lactam, using the desired acid or base; or
 (iii) by converting one salt of the compound of formula (1) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionization in the resulting salt may vary from completely ionized to almost non-ionized.

The compounds of the invention may exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water. Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components, which may be in stoichiometric or non-stoichiometric amounts. The resulting complexes may be ionised, partially ionized, or non-ionized. For a review of such complexes, see J Pharm Sci, 64 (8), 1269-1288 by Haleblian (August 1975).

Hereinafter all references to compounds of formula (1) include references to salts, solvates and complexes thereof and to solvates and complexes of salts thereof.

The compounds of the invention include compounds of formula (1) as hereinbefore defined, including all polymorphs and crystal habits thereof, prodrugs and isomers thereof (including optical, geometric and tautomeric isomers) as hereinafter defined and isotopically-labeled compounds of formula (1).

As indicated, so-called 'pro-drugs' of the compounds of formula (1) are also within the scope of the invention. Thus certain derivatives of compounds of formula (1) which may have little or no pharmacological activity themselves can, when administered into or onto the body, be converted into compounds of formula (1) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T. Higuchi and W. Stella) and 'Bioreversible Carriers in Drug Design', Pergamon Press, 1987 (ed. E. B Roche, American Pharmaceutical Association).

Prodrugs in accordance with the invention can, for example, be produced by replacing appropriate functionalities present in the compounds of formula (1) with certain moieties known to those skilled in the art as 'pro-moieties' as described, for example, in "Design of Prodrugs" by H. Bundgaard (Elsevier, 1985).

Some examples of prodrugs in accordance with the invention include:
(i) where the compound of formula (1) contains a carboxylic acid functionality (—COOH), an ester thereof, for example, a compound wherein the hydrogen of the carboxylic acid functionality of the compound of formula (1) is replaced by (C1-C8)alkyl;
(ii) where the compound of formula (1) contains an alcohol functionality (—OH), an ether thereof, for example, a compound wherein the hydrogen of the alcohol functionality of the compound of formula (1) is replaced by (C1-C6)alkanoyloxymethyl; and
(iii) where the compound of formula (1) contains a primary or secondary amino functionality, an amide thereof, for example, a compound wherein, as the case may be, one or both hydrogens of the amino functionality of the compound of formula (1) is/are replaced by $(C_1-C_{10})$alkanoyl.

Further examples of replacement groups in accordance with the foregoing examples and examples of other prodrug types may be found in the aforementioned references. Moreover, certain compounds of formula (1) may themselves act as prodrugs of other compounds of formula (1).

Also included within the scope of the invention are metabolites of compounds of formula (1), that is, compounds formed in vivo upon administration of the drug. Some examples of metabolites in accordance with the invention include
(i) where the compound of formula (1) contains a methyl group, an hydroxymethyl derivative thereof;
(ii) where the compound of formula (1) contains an alkoxy group, an hydroxy derivative thereof;
(iii) where the compound of formula (1) contains a tertiary amino group, a secondary amino derivative thereof;
(iv) where the compound of formula (1) contains a secondary amino group, a primary derivative thereof;
(v) where the compound of formula (1) contains a phenyl moiety, a phenol derivative thereof; and
(vi) where the compound of formula (1) contains an amide group, a carboxylic acid derivative thereof.

Compounds of formula (1) containing one or more asymmetric carbon atoms can exist as two or more stereoisomers. Included within the scope of the present invention are all stereoisomers, geometric isomers and tautomeric forms of the compounds of formula (1), including compounds exhibiting more than one type of isomerism, and mixtures of one or more thereof. Also included is acid addition or base salts wherein the counter ion is optically active, for example, d-lactate or 1-lysine, or racemic, for example, dl-tartrate or dl-arginine. Conventional techniques for the preparation/isolation of individual enantiomers include chiral synthesis from a suitable optically pure precursor or resolution of the racemate (or the racemate of a salt or derivative) using, for example, chiral high-pressure liquid chromatography (HPLC).

Alternatively, the racemate (or a racemic precursor) may be reacted with a suitable optically active compound, for example, an alcohol, or, in the case where the compound of formula (1) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC (chiral columns), on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. For reverse HPLC $CH_3CN$ and $H_2O$, MeOH or iPrOH and $H_2O$ are used as solvents. Concentration of the eluate affords the enriched mixture.

Stereoisomeric conglomerates may be separated by conventional techniques known to those skilled in the art-see, for example, "Stereochemistry of Organic Compounds" by E. L. Eliel (Wiley, New York, 1994). "Chiral Separation Techniques". by G. Subramanian. John Wiley & Sons, 2008. "Preparative Enantioselective Chromatography" by G. B. Cox. Wiley, 2005.

Pharmaceutically acceptable solvates in accordance with the invention include those wherein the solvent of crystallization may be isotopically substituted, e.g. $D_2O$. The compounds of formula (1), their pharmaceutically acceptable salts and/or derived forms, are valuable pharmaceutically active compounds, which are suitable for the therapy and prophylaxis of various cancers, in particular melanoma, breast, prostate and colon Compounds of the invention may be administered as crystalline or amorphous products. They may be obtained, for example, as solid plugs, powders, or films by methods such as precipitation, crystallization, freeze-drying, spray drying, or evaporative drying. Microwave or radio frequency drying may be used for this purpose. They may be administered alone or in combination with one or more other compounds of the invention or in combination with one or more other drugs (or as any combination thereof). Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form. Pharmaceutical compositions suitable for the delivery of compounds of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

The compounds of the invention may be administered by any suitable route.

Thus, a compound of the invention may be formulated as a pharmaceutical composition for oral, buccal, intranasal, parenteral (e. g., intravenous, intramuscular or subcutaneous), topical, or rectal administration or in a form suitable for administration by inhalation or insufflation. For oral administration, the pharmaceutical composition may take the form of, for example, a tablet or capsule prepared by conventional means with a pharmaceutically acceptable excipient such as a binding agent (e. g., pregelatinized maize starch, polyvinylpyrrolidone or hydroxypropyl methylcellulose); filler (e. g., lactose, microcrystalline cellulose or calcium phosphate); lubricant (e. g., magnesium stearate, talc or silica); disintegrant (e. g., potato starch or sodium starch glycolate); or wetting agent (e. g., sodium lauryl sulphate). The tablets may be coated by methods well known in the art. Liquid preparations for oral administration may take the form of a, for example, solution, syrup or suspension, or they may be presented as a dry product for constitution with water or other suitable vehicle before use.

Such liquid preparations may be prepared by conventional means with a pharmaceutically acceptable additive such as a suspending agent (e. g., sorbitol syrup, methyl cellulose or hydrogenated edible fats); emulsifying agent (e. g., lecithin or acacia); non-aqueous vehicle (e. g., almond oil, oily esters or ethyl alcohol); and preservative (e. g., methyl or propyl p-hydroxybenzoates or sorbic acid).

For buccal administration, the composition may take the form of tablets or lozenges formulated in conventional manner. A compound of the present invention may also be formulated for sustained delivery according to methods well known to those of ordinary skill in the art.

Examples of such formulations can be found in U.S. Pat. Nos. 3,538,214, 4,060,598, 4,173,626, 3,119,742, and 3,492,397, which are herein incorporated by reference in their entirety.

A compound of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain a formulating agent such as a suspending, stabilizing and/or dispersing agent. Alternatively, the active ingredient may be in powder form for reconstitution with a suitable vehicle, e. g., sterile pyrogen-free water, before use Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

Inasmuch as it may be desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions. Thus, the kit of the invention comprises two or more separate pharmaceutical compositions, at least one of which contains a compound of formula (1) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example parenteral, for administering the separate compositions at different dosage intervals, or for titrating the separate compositions against one another. To assist compliance, the kit typically comprises directions for administration and may be provided with a so-called memory aid.

For administration to human patients, the total daily dose of the compounds of the invention is typically in the range 0.001 mg to 5000 mg depending, of course, on the mode of administration. For example, an intravenous daily dose may only require from 0.001 mg to 40 mg. The total daily dose may be administered in single or divided doses and may, at the physician's discretion, fall outside of the typical range given herein.

These dosages are based on an average human subject having a weight of about 65 kg to 70 kg. The physician will readily be able to determine doses for subjects whose weight falls outside this range, such as infants and the elderly.

For the avoidance of doubt, references herein to "treatment" include references to curative, palliative and prophylactic treatment.

According to another embodiment of the present invention, the compounds of the formula (1), or pharmaceutically acceptable salts, derived forms or compositions thereof, can also be used as a combination with one or more additional therapeutic agents to be co-administered to a patient to obtain some particularly desired therapeutic end result such as the treatment of cancers namely melanoma, breast, prostate and colon cancer.

The second and more additional therapeutic agents may also be a compound of the formula (1) to (3), or a pharmaceutically acceptable salt, derived forms or compositions thereof, or one or more compounds known in the art for the treatment of the conditions listed above. More typically, the second and more therapeutic agents will be selected from a different class of therapeutic agents.

As used herein, the terms "co-administration", "co-administered" and "in combination with", referring to the compounds of formula (1) and one or more other therapeutic agents, is intended to mean, and does refer to and include the following: simultaneous administration of such combination of compound(s) of formula (1) to (3) and therapeutic agent(s) to a patient in need of treatment, when such components are formulated together into a single dosage form which releases said components at substantially the same time to said patient, substantially simultaneous administration of such combination of compound(s) of formula (1) and therapeutic agent(s) to a patient in need of treatment, when such components are formulated apart from each other into separate dosage forms which are taken at substantially the same time by said patient, whereupon said components are released at substantially the same time to said patient, sequential administration of such combination compound(s) of formula (1) and therapeutic agent(s) to a patient in need of treatment, when such components are formulated apart from each other into separate dosage forms which are taken at consecutive times by said patient with a significant time interval between each administration, whereupon said components are released at substantially different times to said patient; and sequential administration of such combination of compound(s) of formula (1) and therapeutic agent(s) to a patient in need of treatment, when such components are formulated together into a single dosage form which releases said components in a controlled manner whereupon they are concurrently, consecutively, and/or administered at the same and/or different times by said patient, where each part may be administered by either the same or different route. Suitable examples of other therapeutic agents which may be used in combination with the compound(s) of formula (1), or pharmaceutically acceptable salts, derived forms or compositions thereof, include, but are by no means limited to:

Anti cancer agents used for the therapy of cancers such as dacarbazine,

Nitrosourea alkylating agents, such as fotemustine

BRAF inhibitors such as vemurafenib or dabrafenib,

MEK inhibitors such as trametinib,

Anti-CTLA4 antibodies, namely ipilimumab

It is to be appreciated that all references herein to treatment include curative, palliative and prophylactic treatment. The description, which follows, concerns the therapeutic applications to which the compounds of formula (1) to (3) may be put. A still further aspect of the present invention also relates to the use of the compounds of formula (1) to (3), or pharmaceutically acceptable salts, derived forms or compositions thereof, for the manufacture of a drug having an anticancer activity. In particular, the present inventions concerns the use of the compounds of formula (1) to (3), or pharmaceutically acceptable salts, derived forms or compositions thereof, for the manufacture of a drug for the treatment of melanoma. As a consequence, the present invention provides a particularly interesting method to treat a mammal, including a human being, with an effective amount of a compound of formula (1) to (3), or a pharmaceutically acceptable salt, derived form or composition thereof. More precisely, the present invention provides a particularly interesting method for the treatment of a cancer disease in a mammal, including a human being, in particular the diseases and/or conditions listed above, comprising administering said mammal with an effective amount of a compound of formula (1), its pharmaceutically acceptable salts and/or derived forms. The following examples illustrate the preparation of the compounds of the formula (1) and their pharmacological properties

FIGURES

FIG. 1: HA15 inhibits cell viability of melanoma cells and other types of cancer cells.

Cell viability was assessed by measuring the number of cells alive in samples of two different kind of prostate cells, respectively noted LNCAP and PC3, of breast cells noted MCF7, of colon cells noted HT29, of metastatic melanoma cell lines A375 and of melanoma cells from patients noted GIC. The measure of cell viability as performed by cell counting using the trypan blue exclusion method. Results were expressed as the percentage of cells alive relatively to the number of living cells in the presence of DMSO, which corresponds to the negative control associated to the 100% value.

Figure 2:
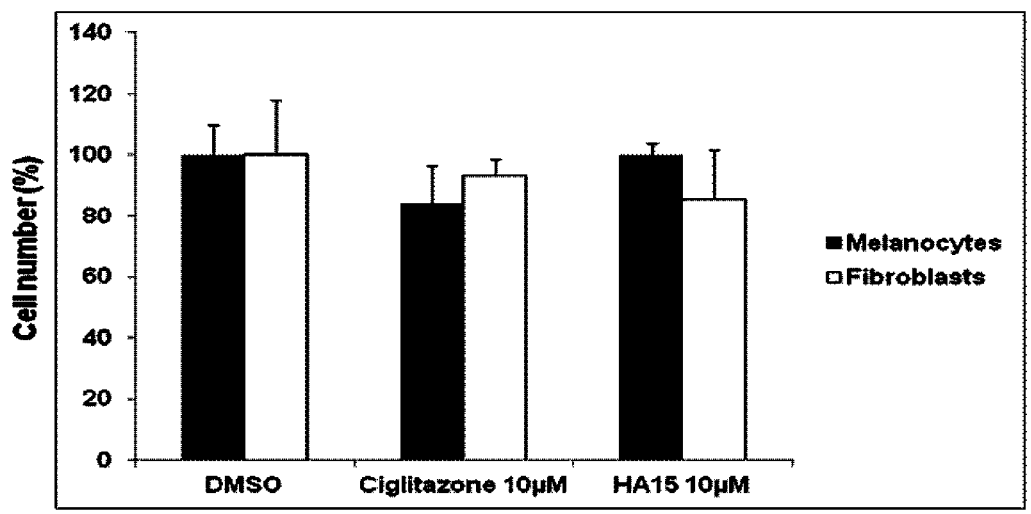

FIG. 2: HA15 does not inhibit cell viability of normal cells.

Primary cell cultures of human normal melanocytes were prepared from human foreskin. In order to determine the effect of compound HA15 on cell viability of melanocytes and fibroblasts, 10 µM of ciglitazone or 10 µM of HA15 were added to the cell samples. The measure of cell viability was performed in the same way as for FIG. 1. Results are expressed as the percentage of living cells relatively to the number of living cells in the presence of DMSO, as for FIG. 1.

Figure 3:
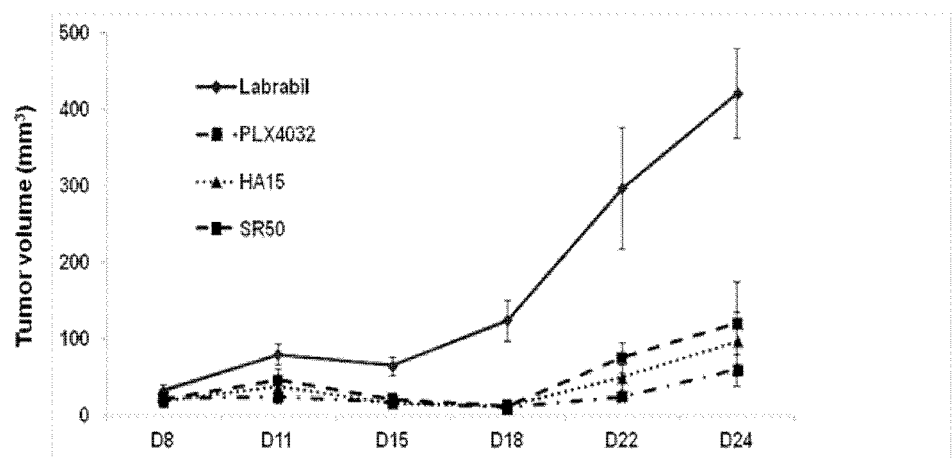

FIG. 3: [HA15] and [SR50] inhibit tumor development in the mouse

To assess a potential antineoplastic effect of (HA15) and (SR50) in vivo, A375 melanoma cells ($2.5 \times 10^6$) were injected subcutaneously in 6-week-old female athymic nude mice and treated 5 days later by injection of vehicle (labrafil) or different compounds such as PLX4032, (HA15) and (SR50) (0.7 mg/mouse/day) over a period of 24 days. Inhibitory effect is expressed as the tumor volume ($mm^3$) on day 8, 11, 15, 18, 22 and 24.

Figure 4:
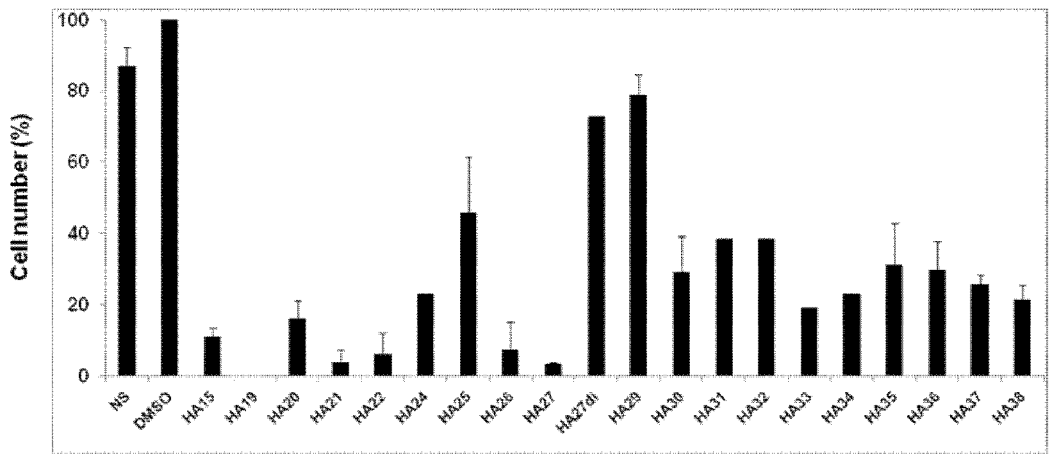

FIG. 4: The effect of compounds [HA15], [HA19], [HA20], [HA21], [HA22], [HA24], [HA25], [HA26], [HA21], [HA27], [HA27di], [HA29], [HA30], [HA31], [HA32], [HA33], [HA34], [HA35], [HA36], [HA37] and [HA38] on cell viability on A375 melanoma cells.

The measure of cell viability was performed in the same way as for FIG. 1. Results are expressed as the percentage of cells alive relatively to the number of living cells in the presence of DMSO, which is a negative control, as for FIG. 1.

Figure 5:
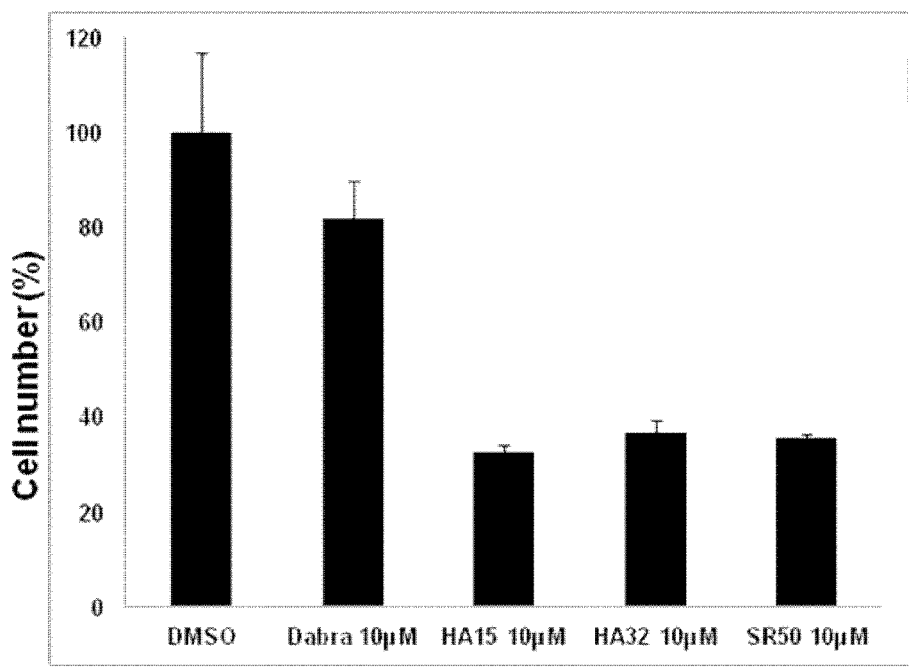
Figure 6:
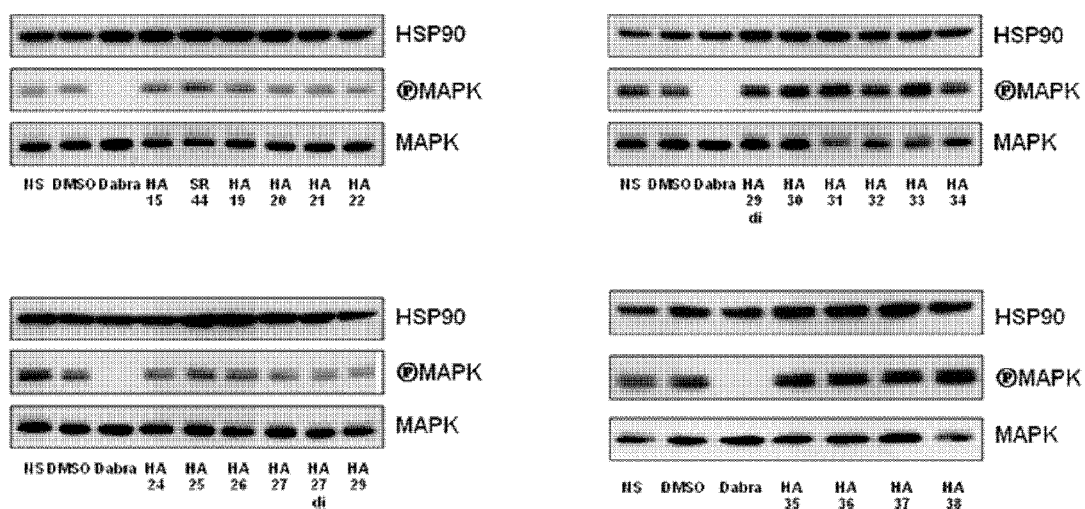

FIG. 5: [HA15], [HA32] and [SR50] inhibit viability of cells resistant to dabrafenib The measure of cell viability was performed in the same way as for FIG. 1. Results are expressed as percentage of cells alive relatively to the number of living cells in the presence of DMSO, which is a negative control FIG. 6: Western Blots showing the effect of compounds of the invention and dabrafenib on MAP Vemurafenib activation on A375 melanoma cells.

EXAMPLES

Chemical Synthesis and Characterization $^1$H and $^{13}$C NMR spectra were recorded on 200 or 500 Burker Advance Spectrometers (200 or 500 MHz for $^1$H, 50 for $^{13}$C). Chemical shifts are expressed as parts per million from tetramethylsilane. Splitting patterns have been designated as follows: s (singlet), d (doublet), t (triplet), m (multiplet) and br (broad). Coupling constants (J values) are listed in hertz (Hz). Analytical thin-layer chromatography (TLC) was conducted on Merck (VWR) precoated silica gel 60F254 plates and compounds were visualized with ninhydrin test and/or under ultraviolet light (254 nm). Column chromatographies were carried out on silica gel (Merck, 40-63 µm). Electrospray ionization spectrometry (ESI-MS) in positive mode was performed on a Burker Daltonics (Esquire 3000 plus) apparatus. HPLC analyses were recorded on waters instruments using columns with different sizes.

Example 1

Preparation of 5-(dimethylamino)-N-(3-(2-(methylamino)thiazol-4-yl)phenyl)naphthalene-1-sulfonamide (Ia$_1$)

1. Preparation of 2-Bromo-1-(3'-nitrophenyl)ethanone (1a$_1$, R$_5$=H)

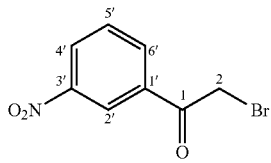

5% of aluminium chloride (160 mg) was added to a suspension of commercially available 3-nitroacetophenone (4 g, 24.2 mmol) in diethyl ether (25 mL) and the reaction mixture was placed at 0° C. Then, bromine (1 eq., 1.4 mL, 24.2 mmol) was added dropwise. The reaction was stirred for 1 h at room temperature until complete consumption of starting material. After addition of water (30 mL), the mixture was extracted with diethyl ether (3×30 mL). The product (2) was obtained as a yellow solid and used in the following reaction without further purification: yield 5.7 g (97%); SM (ESI) m/z=266 [M+Na]$^+$; $^1$H NMR (CDCl$_3$, 200 MHz): δ 4.42 (s, 2H, CH$_2$), 7.67 (t, 1H, J=8 Hz, H$_5$'), 8.26 (ddd, 1H, J=8 Hz, J=1.6 Hz, J=1.1 Hz, H$_6$'), 8.40 (ddd, 1H, J=8 Hz, J=2 Hz, J=1.1 Hz, H$_4$'), 8.74 (t, 1H, J=1.2 Hz, H$_2$'); $^{13}$C NMR (CDCl$_3$, 50 MHz): δ 29.9 (CH$_2$), 123.8 (C$_{Ar}$), 128.1 (C$_{Ar}$), 130.2 (C$_{Ar}$), 134.4 (C$_{Ar}$), 135.1 (C$_{Ar}$), 148.5 (C$_{Ar}$), 189.3 (C$_{carbonyl}$).

2. Preparation of 5-(Dimethylamino)-N-(3-(2-(methylamino)thiazol-4-yl)phenyl)naphtalene-1-sulfonamide (Ia$_1$/HA19)

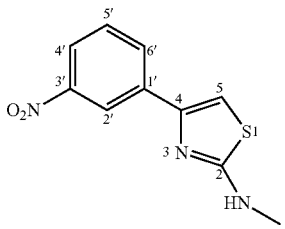 [SMILES: CNc1nc(-c2cccc([N+](=O)[O-])c2)cs1]

N-methylthiourea (1 equiv) was added to a solution of 1-bromo-3-nitroacetophenone (10 mmol) in ethanol (60 mL). The reaction mixture was stirred at 80° C. for 30 min and then left to cool to room temperature. The precipitate was filtered and washed with an ethanol/ether mixture leading to compound 4a$_4$ (97% yield) obtained as a yellow solid: R$_f$=0.70 (CH$_2$Cl$_2$/MeOH: 9/1); SM (ESI) m/z=258 [M+Na]$^+$; $^1$H NMR (DMSO-d6, 200 MHz) δ: 2.90 (d, 3H, CH$_3$), 7.40 (s, 1H, H$_5$), 7.71 (m, 2H, H$_5$', NH), 8.12 (ddd, 1H, J=8.2, 2.3, 0.9 Hz, H$_6$'), 8.28 (m, 1H, H$_4$'), 8.62 (m, 1H, H$_T$). $^{13}$C NMR (DMSO-d6, 50 MHz) δ: 30.9 (CH$_3$), 103.6 (C$_{Ar}$), 119.9 (C$_{Ar}$), 121.7 (C$_{Ar}$), 129.9 (C$_{Ar}$), 131.6 (C$_{Ar}$), 136.3 (C$_{Ar}$), 147.7 (C$_{Ar}$), 148.1 (C$_{Ar}$), 169.6 (C$_{Ar}$).

3. Preparation of 2-N-methyl-4-(3-aminophenyl)thiazole (5a$_4$)

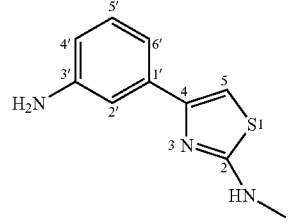

A solution of compound 4a$_4$ (8.0 mmol) in a mixture of acetic acid and ethanol (1:1, v/v, 50 mL) was stirred under a hydrogen atmosphere in the presence of palladium on activated carbon (10%) for 3 h. After removal of the catalyst by filtration through a pad of Celite, the filtrate was concentrated under reduced pressure and the product crystallized in ethyl ether to give a pure compound 5a$_4$ (96% yield) obtained as a white solid: R$_f$=0.58 (CH$_2$Cl$_2$/MeOH: 9/1); SM (ESI) m/z=228 [M+Na]$^+$; $^1$H NMR (DMSO-d6, 200 MHz) δ: 2.85 (d, 3H, CH$_3$), 5.07 (s, 2H, NH2), 6.46 (dt, 1H, J=6.6, 2.4 Hz, H$_5$'), 6.82 (s, 1H, H$_5$), 7.01 (m, 3H, 3H$_{Ar}$), 7.48 (m, 1H, NH)$^{13}$C NMR (DMSO, 50 MHz) δ: 30.98 (CH$_3$), 99.87 (C$_{Ar}$), 111.46 (C$_{Ar}$), 113.1 (C$_{Ar}$), 113.5 (C$_{Ar}$), 128.8 (C$_{Ar}$), 135.5 (C$_{Ar}$), 148.5 (C$_{Ar}$), 151.0 (C$_{Ar}$), 169.0 (C$_{Ar}$).

4. Preparation of 5-(dimethylamino)-N-(3-(2-(methylamino)thiazol-4-yl)phenyl)naphthalene-1-sulfonamide (Ia$_1$)

General Procedure for Amine Sulfonation

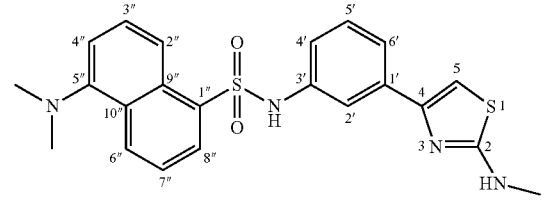

At room temperature and under argon, to a solution of compound (4-(4-aminophenyl)-N-methylthiazol-2-amine, 5a$_4$) (100 mg, 0.49 mmol) in dichloromethane (10 mL) were successively added dansyl chloride (1.2 eq., 137 mg), triethylamine (1.6 eq., 0.11 mL) and DMF (1.5 mL) and the reaction was allowed to run for 24 h. After stirring for 15 h and addition of water (20 mL) the mixture was extracted with EtOAc/water (3×30 mL), the combined organic phases were dried over magnesium sulfate and the solvent evaporated. The crude product was purified on a silica gel column (9:1 to 8:2 cyclohexan-EtOAc) afforded pure compound as a yellow solid: yield (Ia$_1$) 170 mg (79%). R$_f$=0.44 (Cyclohexan/EtOAc: 1/1); SM (ESI) m/z=461 [M+Na]$^+$; $^1$H NMR (DMSO d6, 200 MHz): δ 1.37 (s, 3H, CH$_3$), 2.76 (s, 6H, N(CH$_3$)$_2$), 6.86 (s, 1H, H$_5$), 6.91 (dd, 1H, J=8 Hz, J=1 Hz, KO 7.11 (t, 1H, J=8 Hz, H$_5$'), 7.22 (d, 1H, J=7.32 Hz, H$_{ar}$), 7.34 (d, 1H, J=8 Hz, H$_6$'), 7.52 (t, J=1.7 Hz, H$_2$), 7.56 (m, 3H, 2Har+NH(Me)) 8.23 (d, 1H, J=6.3 Hz, H$_{ar}$), 8.39 (t, 2H, J=8.5 Hz, H$_T$, H$_7$), 10.69 (s, 1H, NH(SO$_2$)); $^{13}$C NMR (DMSO d6, 50 MHz): δ 30.9 (CH$_3$), 44.9 (2C$_{dimethylamino}$), 101.2 (C$_{Ar}$), 115.2 (C$_{Ar}$), 116.2 (C$_{Ar}$), 117.5 (C$_{Ar}$), 118.6 (C$_{Ar}$), 120.5 (C$_{Ar}$), 123.4 (C$_{Ar}$), 128.1 (C$_{Ar}$), 128.9 (C$_{Ar}$), 129.0 (C$_{Ar}$), 129.1 (C$_{Ar}$), 129.8 (C$_{Ar}$), 130.0 (C$_{Ar}$), 134.8 (C$_{Ar}$), 135.6 (C$_{Ar}$), 137.8 (C$_{Ar}$), 149.4 (C$_{Ar}$), 151.4 (C$_{Ar}$), 169.2 (C$_{thiazol(2)}$)

Example 2

Preparation of N-(4-(3-5-Naphtalene-2-sulfonamido)phenyl)thiazol-2yl)acetamide (Ia$_2$/HA26)

1. Preparation of 2-Bromo-1-(3'-nitrophenyl)ethanone (1a$_1$, R$_5$=H)

The compound was prepared according to the same procedure as for Example 1.

2. Preparation of N-(4-(3'-Nitrophenyl)thiazol-2-yl)acetamide (4a$_1$, R$_5$=H, R$_3$, R$_4$=H, Ac)

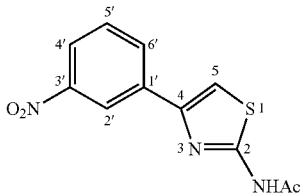

To a solution of 1-bromo-3-nitroacetophenone (1a$_1$, R$_5$=H) (2.6 g, 10.6 mmol) in ethanol (70 mL) was added the N-acetylthiourea (1 eq., 1.25 g, 10.6 mmol). The reaction mixture was then stirred at 80° C. for 30 min. then left to cool to room temperature. The precipitate was filtered and washed with 1:1 ethanol-ether solution affording compound (4a$_1$) as a yellow solid and employed in the following reaction without further purification: yield 2.4 g (84%). R$_f$=0.55 (cyclohexane/EtOAc: 1/1); SM (ESI) m/z=266 [M+Na]$^+$; $^1$H NMR (DMSO-d6, 200 MHz): δ 2.15 (s, 3H, CH$_3$), 7.70 (t, 1H, J=8 Hz, H$_5$'), 7.90 (s, 1H, H$_5$), 8.15 (ddd, 1H, J=1 Hz; J=2.2 Hz; J=8 Hz, H$_6$'), 8.31 (ddd, 1H, J=8 Hz, J=1.2 Hz, J=2.2 Hz, H$_4$'), 8.72 (s, 1H, H$_2$'), 12.35 (s, 1H, NH); $^{13}$C NMR (DMSO-d6, 50 MHz): δ 22.4 (CH3), 110.37 (C$_{Ar}$), 119.97 (C$_{Ar}$), 122.20 (C$_{Ar}$), 130.31 (C$_{Ar}$), 131.65 (C$_{Ar}$), 135.75 (C$_{Ar}$), 146.19 (C$_{Ar}$), 148.27 (C$_{Ar}$), 158.37 (C$_{Ar}$), 168.75 (C$_{carbonyl}$).

3. Preparation of N-(4-(3'-Aminophenyl)thiazol-2-yl)acetamide (5a$_1$, R$_5$=H, R$_3$, R$_4$=H, Ac)

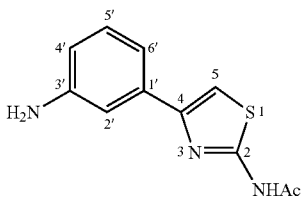 [SMILES: CC(=O)Nc1nc(-c2cccc(N)c2)cs1]

General Procedure for Reduction of NO$_2$:
To a mixture containing (4a$_1$, R$_5$=H, R$_3$, R$_4$=H, Ac) (2.2 g, 8.35 mmol) and palladium on activated carbon (10%) at 0° C. was added NaBH$_4$ (5 eq. 1.58 g, 41.75 mmol) in a mixture of 1:1 dichloromethane-methanol (35 mL) and the reaction mixture was stirred for 5 h. After filtration through a pad of Celite, the filtrate was concentrated under reduced pressure and the crude material was purified by silica gel column (99:1 to 95:5 CH$_2$Cl$_2$-MeOH) to give pure compound (5a$_1$) as a white solid: yield 974 mg (50%); R$_f$=0.25 (cyclohexane/EtOAc: 1/1); SM (ESI) m/z=256 [M+Na]$^+$; $^1$H NMR (DMSO d6, 200 MHz): δ 2.13 (s, 3H, CH$_3$), 5.12 (s, 2H, NH$_2$), 6.50 (dt, 1H, J=6.44 Hz, J=2.4 Hz, H$_4$'), 7.03 (m, 2H, H$_6$' and H$_5$'), 7.34 (s, 1H, H$_5$), 7.93 (s, 1H, H$_2$'), 12.22 (s, 1H, NH); $^{13}$C NMR (DMSO-d6, 50 MHz): δ 22.4 (CH$_3$), 106.8 (C$_{Ar}$), 111.2 (C$_{Ar}$), 113.5 (C$_{Ar}$), 129.1 (C$_{Ar}$), 134.8 (C$_{Ar}$), 148.8 (C$_{Ar}$), 149.5 (C$_{Ar}$), 157.5 (C$_{Ar}$), 162.2 (C$_{Ar}$), 168.5 (C$_{carbonyl}$)

4. Preparation of N-(4-(3-5-Naphtalene-2-sulfonamido)phenyl)thiazol-2yl)acetamide (Ia$_2$/HA26)

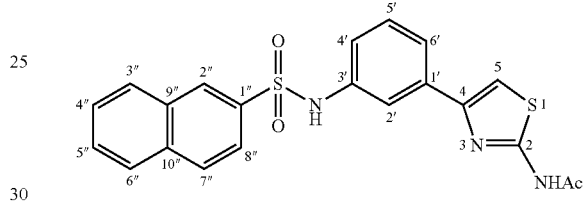

According to procedure 3, compound (5a$_1$) (80 mg, 0.34 mmol) in dichloromethane (10 mL), 2-naphtalenesulfonyl chloride (1.2 eq., 93.3 mg), triethylamine (1.6 eq., 0.075 mL) and DMF (2 mL), after treatment and purification, afforded (Ia$_2$) as a white solid. Yield 84.7 mg (60%); R$_f$=0.38 (Cyclohexan/EtOAc: 1/1); SM (ESI) m/z=446 [M+Na]$^+$; $^1$H NMR (DMSO d6, 200 MHz): δ 2.14 (s, 3H, CH$_3$), 7.01 (dd, 1H, J=8 Hz, J=1.2 Hz, H$_4$'), 7.21 (t, 1H, J=8 Hz, H$_5$'), 7.45 (s, 1H, H$_5$), 7.48 (d, 1H, J=8 Hz, H$_6$'), 7.63 (m, 2H, 2H$_{ar}$), 7.70 (t, 1H, J=1.7 Hz, H$_2$'), 7.76 (dd, 1H, J=8.6 Hz, J=1.8 Hz, H$_{ar}$), 7.96 (m, 1H, H$_{ar}$), 8.06 (m, 2H, 2H$_{ar}$), 8.43 (s, 1H, H$_{ar}$), 10.48 (s, 1H, NH(SO$_2$)), 12.24 (s, 1H, NH(Ac)); $^{13}$C NMR (DMSO d6, 50 MHz): δ 22.4 (CH$_3$), 108.3 (C$_{Ar}$), 117.5 (C$_{Ar}$), 119.5 (C$_{Ar}$), 121.5 (C$_{Ar}$), 121.9 (C$_{Ar}$), 127.6 (C$_{Ar}$), 127.7 (C$_{Ar}$), 127.9 (C$_{Ar}$), 128.9 (C$_{Ar}$), 129.1 (C$_{Ar}$), 129.4 (C$_{Ar}$), 131.4 (C$_{Ar}$), 134.1 (C$_{Ar}$), 135.1 (C$_{Ar}$), 136.3 (C$_{Ar}$), 138.0 (2C$_{Ar}$), 147.9 (C$_{Ar}$), 157.9 (C$_{Ar}$), 168.7 (C$_{carbonyl}$)

Example 3

Preparation of N-(4-(3'-(2'''-Fluorophenylsulfonamido)phenyl)thiazol-2-yl)acetamide (Ia$_3$/HA 25)

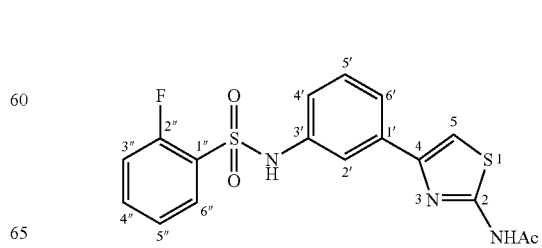

According to procedure 3, compound (5a₁) (80 mg, 0.34 mmol) in dichloromethane (10 mL), 2-fluorobenzene-1-sulfonyl (1.2 eq., 79.4 mg), triethylamine (1.6 eq, 0.075 mL) and DMF (2 mL), after treatment and purification, afforded (4b₃) as a white solid. Yield 105.7 mg (80%); $R_f$=0.38 (cyclohexane/EtOAc: 1/1); SM (ESI) m/z=414 [M+Na]⁺; ¹H NMR (DMSO d6, 200 MHz): δ 2.14 (s, 3H, CH3), 7.03 (dd, 1H, J=1.2 Hz, J=8 Hz, $H_{4'}$), 7.25 (t, 1H, J=8 Hz, $H_{5'}$), 7.32 (td, 1H, J=7.7 Hz, J=1 Hz, HO, 7.39 (td, 1H, J=7.7 Hz, J=1 Hz, $H_{3''}$), 7.45 (s, 1H, $H_5$), 7.52 (d, 1H, J=8 Hz, $H_{6'}$), 7.61 (m, 1H, $H_{Ar}$), 7.68 (t, 1H, J=1.8 Hz, $H_{2'}$), 7.82 (td, 1H, J=7.6 Hz, J=2 Hz, $H_{4''}$), 10.69 (s, 1H, NH(SO₂)), 12.25 (s, 1H, NH(Ac)); ¹³C NMR (DMSO d6, 50 MHz): δ 22.4 (CH3), 108.4 ($C_{Ar}$), 117.0 ($C_{Ar}$), 117.2 ($C_{Ar}$), 117.4 ($C_{Ar}$), 119.2 ($C_{Ar}$), 121.6 ($C_{Ar}$), 124.8 ($C_{Ar}$), 126.7 ($C_{Ar}$), 126.9 ($C_{Ar}$), 129.5 ($C_{Ar}$), 130.4 ($C_{Ar}$), 135.2 ($C_{Ar}$), 137.5 ($C_{Ar}$), 147.9 ($C_{Ar}$), 157.9 ($C_{Ar}$), 168.7 ($C_{carbonyl}$).

Example 4

Preparation of N-(4-(3-(3-(Trifluoromethylphenyl-sulfonamido)-phenyl)thiazol-2-yl)acetamide: (Ia₄)

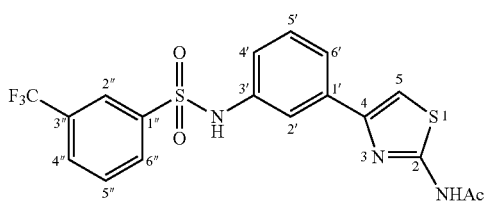

According to procedure 3 compound (5a₁) (100 mg, mmol) in dichloromethane (10 mL), 3-(trifluoromethyl)benzene-1-sulfonyl chloride (1.2 eq., 0.083 mL), triethylamine (1.6 eq., 0.096 mL) and DMF (2 mL), after treatment and purification, afforded (Ia₄) as a white solid yield 46.7 mg (24%); $R_f$=0.3 (cyclohexane/EtOAc: 1/1); SM (ESI) m/z=464 [M+Na]⁺; ¹H NMR (DMSO d6, 200 MHz): δ 2.14 (s, 3H, CH₃), 6.97 (dd, 1H, J=8 Hz, J=1.3 Hz, $H_{4'}$), 7.27 (t, 1H, J=8 Hz, $H_{5'}$), 7.49 (s, 1H, $H_5$), 7.57 (d, 1H, 8 Hz, $H_{6'}$), 7.70 (t, 1H, J=1.6 Hz, $H_{2'}$), 7.78 (m, 1H, $H_{ar}$), 7.99 (m, 3H, 3$H_{ar}$), 10.5 (s, 1H, NH(SO₂)), 12.25 (s, 1H, NHAc); ¹³C NMR (DMSO d6, 50 MHz): δ 22.4 (CH₃), 108.5 ($C_{Ar}$), 118.2 ($C_{Ar}$), 120.1 ($C_A$), 120.5 ($C_{Ar}$), 122.1 ($C_{Ar}$), 123.1 ($C_{Ar}$), 129.4 ($C_{Ar}$), 129.6 ($C_{Ar}$), 130.1 ($C_{Ar}$), 130.5 ($C_{Ar}$), 131.0 ($C_{Ar}$), 135.3 ($C_{Ar}$), 137.4 ($C_{phenyl(3')}$), 140.4 ($C_{Ar}$), 147.8 ($C_{Ar}$), 158.0 ($C_{Ar}$), 168.7 ($C_{carbonyl}$).

Example 5

Preparation of N-(4-(4'-(2'',4''-Difluorophenylsulfonamido)phenyl)thiazol-2-yl)acetamide (Ib₁)

1. Preparation of 2-N-Acetylamino-4-(4-nitrophenyl)thiazole (4b₁)

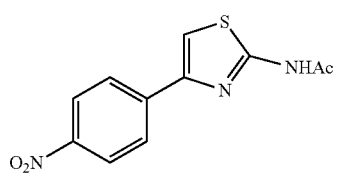 [SMILES: CC(=O)Nc1nc(-c2ccc([N+](=O)[O-])cc2)cs1]

To a solution of 1-bromo-4-nitroacetophenone (2.5 g, 10 mmol) in ethanol (60 mL) was added the N-acetylthiourea (1 equiv, 1.24 g). The reaction mixture was stirred at 80° C. for 30 min and then left to cool to room temperature. The precipitate was filtered and washed with an ethanol/ether mixture leading to 2.2 g of compound 4b₁ (98% yield) obtained as a yellow solid: $R_f$=0.7 (CH₂Cl₂/MeOH: 9/1); ¹H NMR (DMSO d6, 200 MHz) δ 2.17 (s, 3H), 7.70 (s, 1H), 8.13 (d, 2H, J=9.0), 8.30 (d, 2H, J=9.0); ¹³C NMR (DMSO d6, 50 MHz) δ 22.9, 112.7, 124.6, 126.8, 140.7, 146.8, 146.9, 158.9, 169.2; mass spectrum (ESI) m/z 264.04376 (M+H)⁺ (C₁₁H₁₀N₃O₃S requires m/z 264.04429).

2. Preparation of 2-N-Acetylamino-4-(4-aminophenyl)thiazole (5b₁)

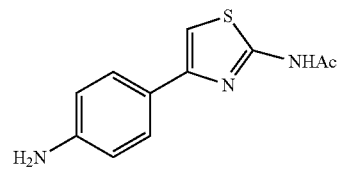

A solution of compound 4b₁ (2.20 g, 8.37 mmol) in a mixture of acetic acid and ethanol (1:1, v/v, 50 mL) was stirred under a hydrogen atmosphere in the presence of palladium on activated carbon (10%) for 3 h. After removal of the catalyst by filtration through a pad of Celite, the filtrate was concentrated under reduced pressure and the product crystallized in ethyl ether to give 1.85 g of pure compound 5b₁ (95% yield) obtained as a white solid: $R_f$=0.54 (CH₂Cl₂/MeOH: 9/1); ¹H NMR (DMSO d6, 200 MHz) δ 2.15 (s, 3H), 5.26-5.28 (br s, 2H), 6.60 (d, 2H, J=8.6), 7.17 (s, 1H), 7.56 (d, 2H, J=8.4); ¹³C NMR (DMSO d6, 50 MHz) δ 22.9, 103.5, 114.1, 122.8, 127.0, 148.9, 150.1, 157.8, 168.7; mass spectrum (ESI) m/z 234.06985 (M+H)⁺ (C₁₁H₁₂N₃OS requires m/z 234.07011).

3. Preparation of Ib₁

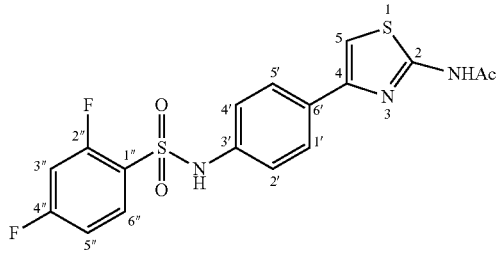

According to procedure 3, compound (5b₁) (50 mg, 0.21 mmol) in dichloromethane (10 mL), 4-difluorobenzene-1-sulfonyl chloride (1.2 eq., 0.034 mL), triethylamine (1.6 eq., 0.047 mL) and DMF (2 mL), after treatment and purification, afforded (Ib₁) as a yellow solid: yield 25 mg (29%); $R_f$=0.33 (cyclohexane/EtOAc: 1/1); SM (ESI) m/z=432 [M+Na]⁺; ¹H NMR (DMSO d6, 200 MHz): δ 2.12 (s, 3H, CH₃), 7.01 (dd, 1H, J=8.6 Hz, $H_{3'}$, $H_{5'}$), 7.23 (tdd, 1H, J=1 Hz, J=2.5 Hz, J=9 Hz, $H_{3''}$), 7.45 (s, 1H, $H_5$), 7.52 (m, 1H, HO, 7.73 (d, 2H, J=8.6 Hz, $H_{2'}$, $H_{6'}$), 7.89 (m, 1H, $H_{ar}$), 10.73 (s, 1H, NH(SO₂)), 12.22 (s, 1H, NH(Ac)); ¹³CNMR (DMSO d6, 50 MHz): δ 22.4 (CH$_3$), 107.2 (C$_{Ar}$), 119.9 (C$_{Ar(3',5')}$), 126.5 (C$_{Ar(2',6')}$), 130.5 (C$_{Ar}$), 136.3 (C$_{Ar}$), 147.9 (C$_{Ar}$), 157.9 (C$_{Ar}$), 168.5 (C$_{carbonyl}$).

Example 6

Preparation of N-(4-(4-(4 (Trifluoromethyl)phenyl-sulfonamido)phenyl) thiazol-2-yl)acetamide (Ib$_2$)

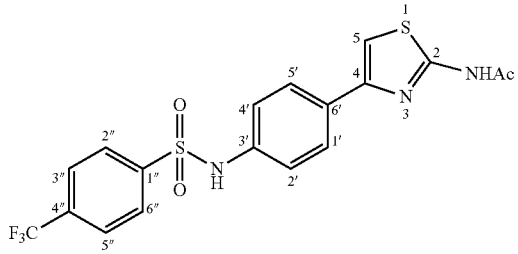

According to procedure 3, compound (5b$_1$) (50 mg, 0.21 mmol) in dichloromethane (10 mL), 4-(trifluoromethyl) benzene-1-sulfonyl chloride (1.2 eq., 61.6 mg), triethylamine (1.6 eq., 0.047 mL) and DMF (2 mL), after treatment and purification, afforded (Ib$_2$) as a white solid: yield 37.2 mg (40%); R$_f$=0.55 (cyclohexane/EtOAc: 1/1); SM (ESI) m/z=464 [M+Na]$^+$, 905 [2M+Na]$^+$; $^1$H RMN (DMSO d6, 200 MHz): δ 2.12 (s, 3H, CH$_3$), 7.12 (d, 2H, J=8.7 Hz, H$_{3''}$, H$_{5'}$), 7.45 (s, 1H, H$_5$), 7.73 (d, 2H, J=8.6 Hz, H$_{2'}$, H$_{6'}$), 7.94 (s, 4H, H$_{2''}$, H$_{3''}$, H$_{5''}$, H$_{6''}$), 10.62 (br, 1H, NH(SO$_2$)), 12.21 (s, 1H, NH(Ac)); $^{13}$C NMR (DMSO d6, 50 MHz): δ 22.4 (CH$_3$), 107.4 (C$_{Ar}$), 120.6 (C$_{Ar}$), 126.0, 126.5, 126.6, 127.7, 130.8, 132.2, 132.8, 147.8, 157.9, 166.3, 168.6 (C$_{carbonyl}$).

Example 7

Preparation of Further Intermediates

7.1. Preparation of 4-(3'-Nitrophenyl)-2-aminothiazole (4a$_2$, R$_5$=H, R$_3$=R$_4$=H)

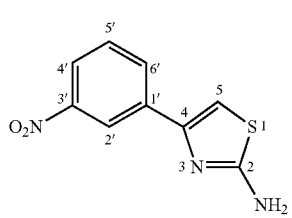

To a solution of 1-Bromo-3-nitroacetophenone (1a$_1$, R$_5$=H) (2.5 g, 10.25 mmol) in ethanol (70 mL) was added thiourea (1 eq., 0.78 g, 10.25 mmol). The reaction mixture was then stirred at 80° C. for 1 h then left to cool to room temperature. The precipitate was filtered and washed with 1:1 ethanol-ether solution affording compound (4a$_2$) as a yellow solid and employed in the following reaction without further purification: yield 2 g (88%). R$_f$=0.6 (cyclohexane-EtOAc: 1/1); SM (ESI) m/z=222 [M+H]$^+$; $^1$H NMR (DMSO d6, 200 MHz): δ 7.47 (s, 1H, H$_5$), 7.73 (t, 1H, J=8 Hz, H$_{5'}$), 8.19 (d, 1H, J=8 Hz, H$_{6'}$), 8.20 (d, 1H, J=8 Hz, H$_{4'}$); 8.56 (t, 1H, J=1.9 Hz, H$_{2'}$), 9.6 (br, 2H, NH$_2$); $^{13}$C NMR (DMSO-d6, 50 MHz): δ 105.1 (C$_{Ar}$), 120.1 (C$_{Ar}$), 122.8 (C$_{Ar}$), 130.3 (C$_{Ar}$), 131.8 (C$_{Ar}$), 133.6 (C$_{Ar}$), 134.8 (C$_{Ar}$), 148.1 (C$_{Ar}$), 169.5 (C$_{Ar}$).

7.2. Preparation of N-(4-(3'-Nitrophenyl)thiazol-2-yl)benzamide (4a$_3$, R$_5$=H, R$_3$=R$_4$=H)

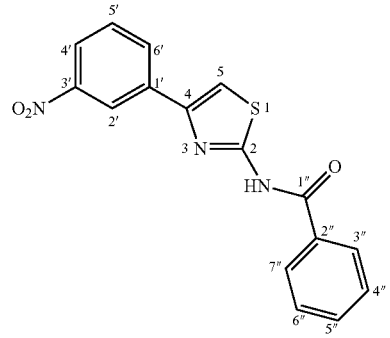

Benzoyl chloride (1.2 eq., 0.31 mL) was added dropwise in a solution of (4a$_2$) (508 mg, 2.29 mmol) in anhydrous pyridine (35 mL) at 0° C. Then benzoly chloride was added (1.2 eq., 0.31 mL). Then the reaction mixture was then left to cool to room temperature for 15 h. Water was added and the mixture was extracted with ethyl acetate (3×30 mL). The combined organic phases were dried over magnesium sulfate and finally the solvent (ethyl acetate and pyridine) was evaporated. The crude product was purified on a silica gel column (9:1 to 8:2 cyclohexane-EtOAc) to give pure compound (4a$_3$) as a white solid: yield 568 mg (76%). R$_f$=0.26 (cyclohexane/EtOAc: 1/1); SM (ESI): m/z=348 [M+Na]$^+$, m/z=673[2M+Na]$^+$; $^1$H NMR: (DMSO d6, 50 MHz): δ 7.54 (m, 3H, H$_{4''}$, H$_{5''}$, H$_{6''}$), 7.72 (t, 1H, J=8 Hz, H$_{5'}$), 7.99 (s, 1H, H5), 8.14 (m, 3H, H$_{6'}$, H$_{2''}$, H$_{7''}$), 8.36 (dt, 1H, J=8 Hz, J=1.5 Hz, H$_{4'}$), 8.79 (t, 1H, J=1.9 Hz, H$_{2'}$), 12.85 (s, 1H, NH); $^{13}$C NMR (DMSO-d6, 50 MHz): δ 111.0 (C$_{Ar}$), 120.1 (C$_{Ar}$), 122.2 (C$_{Ar}$), 128.1 (C$_{benzoyl(3'',7'')}$), 128.5 (C$_{benzoyl(4'',6'')}$), 130.3 (C$_{Ar}$), 131.7 (2C$_{Ar}$), 132.7 (C$_{Ar}$), 135.8 (C$_{Ar}$), 146.6 (C$_{Ar}$), 148.3 (C$_{Ar}$), 158.9 (C$_{Ar}$), 165.3 (C$_{carbonyl}$).

7.3. Preparation of N-(4-(3'-Aminophenyl)thiazol-2-yl)benzamide (5a$_2$, R$_5$=H, R$_3$, R$_4$=H, Ac)

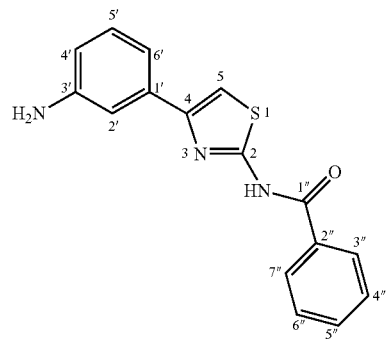 [SMILES: O=C(Nc1nc(-c2cccc([N+](=O)[O-])c2)cs1)c1ccccc1]

The procedure 1 was applied to (4a$_3$) (770 mg, 2.37 mmol) in 1:1 dichloromethane-methanol (30 mL), treated with NaBH$_4$ (5 eq. 450.3 mg, 11.8 mmol) and palladium on activated carbon (10%) [Reaction time: 7 h]. Purification on a silica gel column (7/3 cyclohexane-EtOAc) to give pure compound (5a$_2$) as a white solid: yield 521 mg (75%); R$_f$=0.4 (cyclohexane/EtOAc: 1/1); SM (ESI) m/z=318 [M+Na]$^+$; $^1$H NMR (DMSO d6, 200 MHz): δ 5.22 (br, 2H, NH$_2$), 7.06 (m, 2H, H$_6$, H$_4'$), 7.13 (t, 1H, J=1.4 Hz, H$_2'$), 7.45 (s, 1H, H$_5$), 7.59 (tt, 1H, H$_{5''}$), 7.55 (d, 2H, J=7.32 Hz, H$_{4''}$, H$_{6''}$), 7.53 (m, 1H, H$_{5'}$), 8.11 (dd, 2H, J=8 Hz, J=1.5 Hz, H$_{2'}$, H$_{6'}$), 12.76 (s, 1H, NH); $^{13}$C NMR (DMSO d6, 50 MHz): δ 107.6 (C$_{Ar}$), 111.3 (C$_{Ar}$), 113.5 (C$_{Ar}$), 113.7 (C$_{Ar}$), 128.1 (C$_{benzoyl(3'',7'')}$), 128.5 (C$_{benzoyl(4'',6'')}$), 129.1 (C$_{Ar}$), 132.0 (C$_{Ar}$), 132.5 (C$_{Ar}$), 134.9 (C$_{Ar}$), 148.8 (C$_{Ar}$), 149.9 (C$_{Ar}$), 158.2 (C$_{Ar}$), 165.2 (C$_{carbonyl}$)

The following compounds were prepared using similar procedures to those described above.

| Ex | Chemical structure | Spectral Data (δ in ppm) |
|---|---|---|
| HA15 | 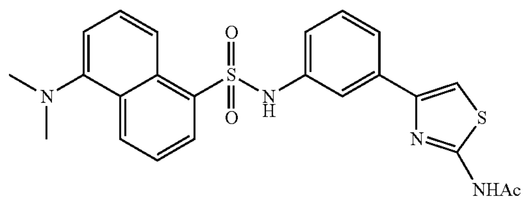 [SMILES: CC(=O)Nc1nc(-c2cccc(NS(=O)(=O)c3cccc4c(N(C)C)cccc34)c2)cs1] | HRMS (ES) m/z = 467.1212 [M + H]$^+$<br>$^1$H NMR (CD$_3$OD, 200 MHz): δ 2.17 (s, 3H, Ac), 2.79 (s, 6H, NMe$_2$), 6.84 (m, 1H, H—Ar), 7.06 (m, 2H, H—Ar), 7.21 (M, 1H, H—Ar), 7.42 (m, 2H, H—Ar), 7.56 (m, 2H, H—Ar), 8.17 (m, 1H, H—Ar), 8.42 (m, 2H, H—Ar).<br>$^{13}$C NMR (CD$_3$OD, 50 MHz): 22.5; 45.8; 108.9; 116.4; 119.3; 120.4; 120.9; 123.0; 124.1; 129.2; 130.2; 131.3; 131.5; 136.1; 136.8; 139.3; 150.4; 153.2; 170.9. |
| HA20 | 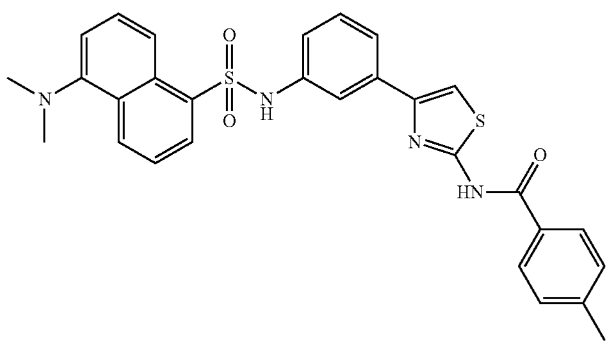 | MS (ESI) m/z = 565 [M + Na]$^+$<br>$^1$H NMR (DMSO-d6, 200 MHz): δ 2.37 (s, 3H, CH3), 2.76 (s, 6H, NMe$_2$), 6.96 (m, 1H, H—Ar), 7.19 (m, 2H, H—Ar), 7.34 (d, 2H, J = 8.0 Hz), 7.48 (m, 2H, H—Ar), 7.61 (m, 3H, H—Ar), 8.1 (d, 2H, J = 8.2 Hz, H—Ar), 8.24 (m, 1H, H—Ar), 8.39 (dd, 2H, J = 8.4, 6.0 Hz, H—Ar), 10.78 (s, 1H, NH), 12.69 (s, 1H, H—Ar)<br>$^{13}$C NMR (DMSO-d6, 50 MHz): 21.03; 44.95; 108.96; 115.21; 116.24; 118.27; 118.60; 121.09; 123.49; 128.19; 128.92; 128.96; 129.06; 129.77; 130.09; 134.70; 135.20; 138.05; 142.83; 148.46; 151.41; 158.60; 165.14. |
| HA21 | 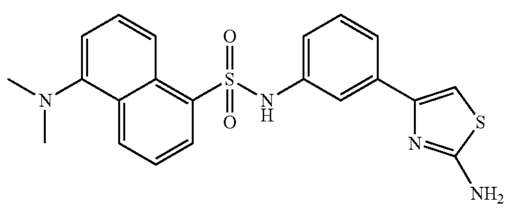 | MS (ESI) m/z = 385 [M + Na]$^+$<br>$^1$H NMR (DMSO-d6, 200 MHz): δ 2.77 (s, 6H, NMe$_2$), 6.80 (s, 1H, H—Ar), 6.91 (m, 1H, H—Ar), 7.14 (m, 1H, H—Ar), 7.30 (m, 2H, H—Ar), 7.49 (s, 1H, H—Ar), 7.59 (td, 2H, J = 8.0, 4.5 Hz, H—Ar), 8.20 (d, 1H, J = 6.6 Hz, H—Ar), 8.38 (t, 2H, J = 8.5 Hz, H—Ar), 10.68 (s, 1H, H—Ar)<br>$^{13}$C NMR (DMSO-d6, 50 MHz): 44.96; 101.88; 115.21; 116.17; 117.41; 118.62; 120.54; 123.47; 128.12; 128.91; 129.06; 130.03; 134.75; 135.65; 137.82; 149.15; 151.39; 168.09. |
| HA24 | 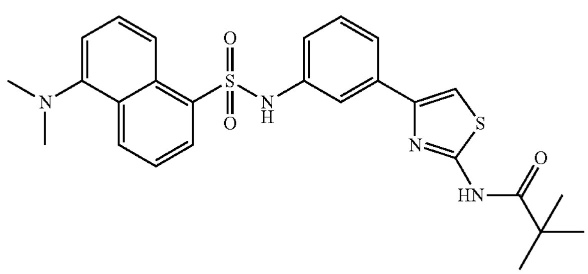 [SMILES: CN(C)c1cccc2c(S(=O)(=O)Nc3cccc(-c4csc(NC(=O)C(C)(C)C)n4)c3)cccc12] | MS (ESI) m/z = 509 [M + H]$^+$<br>$^1$H NMR (DMSO-d6, 200 MHz): δ 1.25 (s, 9H, 3 × CH$_3$), 2.78 (s, 6H, NMe$_2$), 7.12 (m, 3H, H—Ar), 7.38 (m, 1H, H—Ar), 7.58 (m, 4H, H—Ar), 8.25 (m, 1H, H—Ar), 8.40 (t, 2H, J = 8.3 Hz, H—Ar), 10.73 (s, 1H, NH), 11.91 (s, 1H, NH)<br>$^{13}$C NMR (DMSO-d6, 50 MHz): 26.53; 44.96; 108.55; 115.22; 116.31; 118.60; 121.12; 123.48; 128.15; 128.91; 129.38; 129.68; 130.08; 134.73; 135.27; 138.00; 148.17; 151.41; 158.66; 176.86. |
| HA27 | 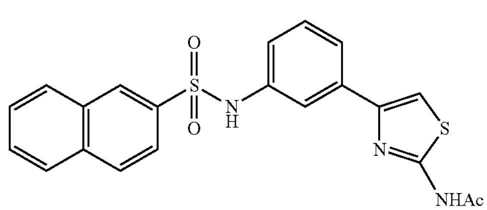 [SMILES: CC(=O)Nc1nc(-c2cccc(NS(=O)(=O)c3ccc4ccccc4c3)c2)cs1] | MS (ESI) m/z = 418 [M + Na]$^+$<br>$^1$H NMR (DMSO-d6, 200 MHz): δ 2.80 (d, 3H, J = 4.7 Hz, CH$_3$), 6.91 (s, 1H, H—Ar), 6.99 (m, 1H, H—Ar), 7.16 (t, 1H, J = 7.8 Hz, H—Ar), 7.37 (m, 1H, H—Ar), 7.60 (m, 2H, H—Ar), 7.75 (m, 2H, H—Ar), 8.05 (m, 2H, H—Ar), 8.44 (m, 1H, H—Ar), 8.56 (m, 1H, H—Ar), 10.42 (s, 1H, NH). |

| Ex | Chemical structure | Spectral Data (δ in ppm) |
|---|---|---|
| HA29 | 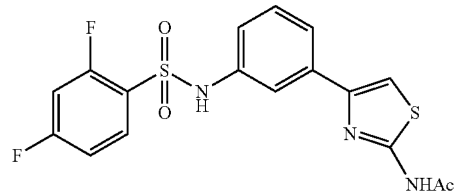 [SMILES: CC(=O)Nc1nc(-c2cccc(NS(=O)(=O)c3ccc(F)cc3F)c2)cs1] | MS (ESI) m/z = 432 [M + Na]+<br>$^1$H NMR (DMSO-d6, 200 MHz): δ 2.17 (s, 3H, Ac), 7.03 (m, 1H, H—Ar), 7.29 (m, 2H, H—Ar), 7.54 (m, 3H, H—Ar), 7.69 (m, 1H, H—Ar), 7.90 (m, 1H, H—Ar), 10.76 (s, 1H, NH), 12.28 (S, 1H, NH).<br>$^{13}$C NMR (DMSO-d6, 50 MHz): 22.43; 108.47; 117.37; 119.40; 121.77; 123.85; 129.53; 135.24; 136.09; 137.34; 147.90; 149.54; 157.97; 168.69. |
| HA37 | 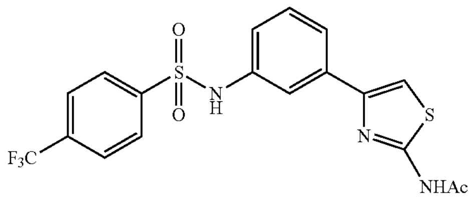 [SMILES: CC(=O)Nc1nc(-c2cccc(NS(=O)(=O)c3ccc(C(F)(F)F)cc3)c2)cs1] | MS (ESI) m/z = 464 [M + Na]+<br>$^1$H NMR (DMSO-d6, 200 MHz): δ 2.16 (s, 3H, Ac), 7.00 (m, 1H, H—Ar), 7.28 (t, 1H, J = 7.9 Hz, H—Ar), 7.56 (m, 2h, H—Ar), 7.71 (s, 1H, H—Ar), 7.95 (s, 4H, H—Ar), 12.26 (s, 1H, NH)<br>$^{13}$C NMR (DMSO-d6, 50 MHz): 22.42; 108.51; 117.93; 119.91; 121.93; 126.48; 127.57; 129.59; 132.12; 132.77; 135.31; 137.65; 143.34; 147.89; 157.98; 168.67. |
| HA32 | 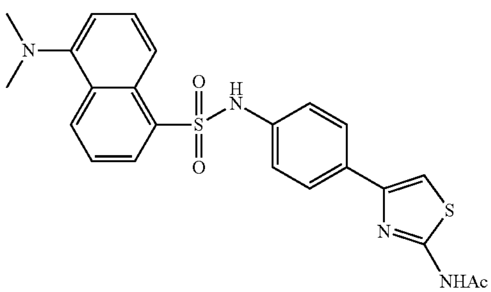 [SMILES: CC(=O)Nc1nc(-c2ccc(NS(=O)(=O)c3cccc4c(N(C)C)cccc34)cc2)cs1] | MS (ESI) m/z = 467 [M + H]+<br>$^1$H NMR (DMSO-d6, 200 MHz): δ 2.12 (s, 3H, NHAc), 2.79 (s, 6H, NMe$_2$), 7.08 (d, 2H, J = 8.7 Hz, H—Ar), 7.24 (d, 1H, J = 7.4 Hz, H—Ar), 7.38 (s, 1H, H—Ar), 7.62 (m, 4H, H—Ar), 8.24 (m, 1H, H—Ar), 8.41 (t, 2H, J = 9.3 Hz, H—Ar), 10.82 (s, 1H, NH), 12.20 (s, 1H, NH).<br>$^{13}$C NMR (DMSO-d6, 50 MHz): 22.39; 44.91; 106.81; 115.20; 118.52; 118.75; 123.42; 126.38; 128.17; 128.91; 129.76; 130.11; 134.66; 137.09; 148.00; 151.40; 157.82; 168.53. |
| HA30 | 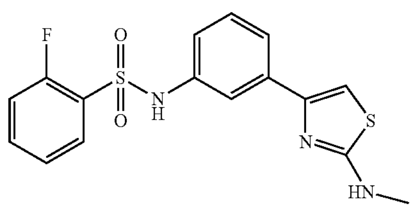 | MS (ESI) m/z = 385 [M + Na]+<br>$^1$H NMR (DMSO-d6, 200 MHz): δ 2.86 (d, 3H, J = 4.7 Hz, CH$_3$), 6.97 (m, 1H, H—Ar), 7.21 (t, 1H, J = 7.9 Hz, H—Ar), 7.41 (m, 3H, H—Ar), 7.63 (m, 3H, H—Ar), 7.85 (m, 1H, H—Ar), 10.66 (s, 1H, NH). |
| HA31 | 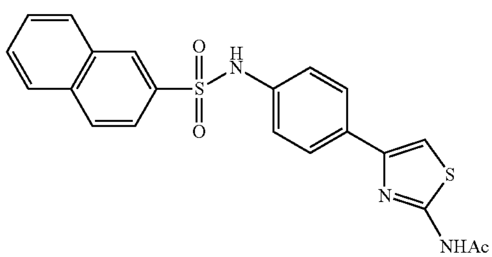 [SMILES: CC(=O)Nc1nc(-c2ccc(NS(=O)(=O)c3ccc4ccccc4c3)cc2)cs1] | MS (ESI) m/z = 426 [M + Na]+<br>$^1$H NMR (DMSO-d6, 200 MHz): δ 2.12 (s, 3H, NHAc), 7.16 (d, 2H, J = 8.5 Hz, H—Ar), 7.40 (s, 1H, H—Ar), 7.71 (m, 5H, H—Ar), 8.06 (m, 3H, H—Ar), 8.46 (s, 1H, H—Ar), 12.20 (s, 1H, NH).<br>$^{13}$C NMR (DMSO-d6, 50 MHz): 22.39; 107.06; 120.07; 121.91; 126.40; 127.66; 127.76; 127.93; 128.94; 129.15; 130.21; 131.45; 134.18; 136.38; 137.05; 147.96; 157.82. |
| HA33 | 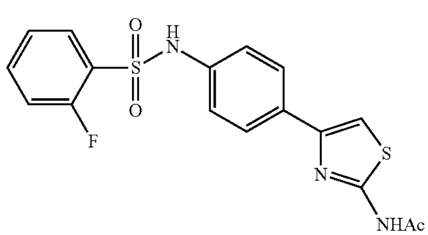 [SMILES: CC(=O)Nc1nc(-c2ccc(NS(=O)(=O)c3ccccc3F)cc2)cs1] | MS (ESI) m/z = 414 [M + Na]+<br>$^1$H NMR (DMSO-d6, 200 MHz): δ 2.14 (s, 3H, NHAc), 7.15 (d, 2H, J = 8.7 Hz, H—Ar), 7.40 (m, 3H, H—Ar), 7.73 (m, 3H, H—Ar), 7.85 (td, 1H, J = 7.6, 1.7 Hz, H—Ar), 10.75 (s, 1H, NH), 12.24 (s, 1H, NH).<br>$^{13}$C NMR (DMSO-d6, 50 MHz): 22.40; 107.15; 119.70; 126.43; 130.31; 130.40; 136.51; 147.95; 157.87; 168.54. |

-continued

| Ex | Chemical structure | Spectral Data (δ in ppm) |
|---|---|---|
| HA35 | 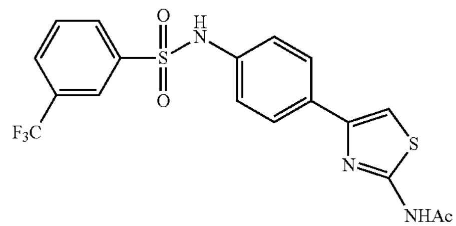 [SMILES: CC(=O)Nc1nc(-c2ccc(NS(=O)(=O)c3cccc(C(F)(F)F)c3)cc2)cs1] | MS (ESI) m/z = 464 [M + Na]⁺<br>¹H NMR (DMSO-d6, 200 MHz): δ 2.15 (s, 3H, NHAc), 7.15 (d, 2H, J = 8.6 Hz, H—Ar), 7.48 (s, 1H, H—Ar), 7.77 (m, 3H, H—Ar), 8.04 (m, 3H, H—Ar), 10.56 (s, 1H, NH), 12.25 (s, 1H, NH)<br>¹³C NMR (DMSO-d6, 50 MHz): 22.40; 107.39; 120.80; 123.14; 126.52; 129+.45; 129.71; 130.10; 130.64; 130.87; 130.95; 136.40; 140.42; 147.85; 157.91; 168.56. |
| JG22A | 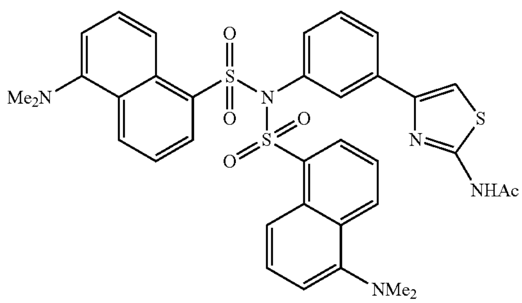 [SMILES: CC(=O)Nc1nc(-c2cccc(N(S(=O)(=O)c3cccc4c(N(C)C)cccc34)S(=O)(=O)c3cccc4c(N(C)C)cccc34)c2)cs1] | MS (ESI) m/z = 722 [M + Na]⁺<br>¹H NMR (DMSO-d6, 200 MHz): δ 2.17 (s, 3H, Ac); 2.83 (s, 12H, 2NMe₂); 6.65 (d, 1H, H—Ar); 7.03-7.32 (m, 5H, H—Ar); 7.40 (s, 1H, H—Ar); 7.50-7.65 (m, 4H, H—Ar); 7.76 (s, 1H, H—Ar); 7.92 (d, 1H, H—Ar); 8.17 (d, 2H, H—Ar); 8.56 (d, 2H, H—Ar); 12.37 (s, 1H, NH).<br>¹³C NMR (DMSO-d6, 50 MHz): 22.40; 30.63; 30.71; 35.70; 44.99; 90.13; 108.83; 115.31; 117.65; 123.44; 127.26; 128.25; 128.61; 129.10; 129.28; 129.55; 130.19; 132.21; 132.54; 132.65; 133.13; 135.30; 146.87; 151.56; 158.19; 168.71. |
| JG24D | 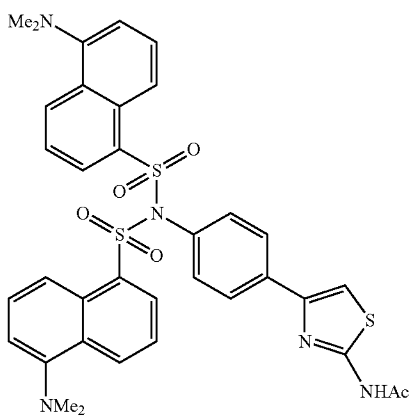 [SMILES: CC(=O)Nc1nc(-c2ccc(N(S(=O)(=O)c3cccc4c(N(C)C)cccc34)S(=O)(=O)c3cccc4c(N(C)C)cccc34)cc2)cs1] | MS (ESI) m/z = 722 [M + Na]⁺<br>¹H NMR (DMSO-d6, 200 MHz): δ 2.16 (s, 3H, Ac); 2.85 (s, 12H, 2NMe₂); 6.97-7.22 (m, 6H, H—Ar); 7.54-7.68 (m, 5H, H—Ar); 7.80 (d, 2H, H—Ar); 8.15 (d, 2H, H—Ar); 8.57 (d, 2H, H—Ar); 12.32 (s, 1H, NH).<br>¹³C NMR (DMSO-d6, 50 MHz): 22.44; 30.61; 44.92; 108.28; 115.19; 116.04; 118.08; 118.59; 120.81; 123.46; 128.15; 128.92; 128.95; 129.39; 129.71; 130.07; 134.68; 135.10; 138.08; 148.02; 151.40; 157.92; 168.65. |
| JG25 | 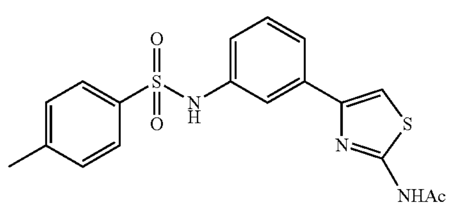 [SMILES: CC(=O)Nc1nc(-c2cccc(NS(=O)(=O)c3ccc(C)cc3)c2)cs1] | MS (ESI) m/z = 410 [M + Na]⁺<br>¹H NMR (DMSO-d6, 200 MHz): δ 2.12 (s, 3H, Ac); 2.31 (s, 6H, Me—Ar); 7.01 (d, 1H, H—Ar); 7.28 (m, 3H, H—Ar); 7.50 (m, 2H, H—Ar); 7.65 (m, 3H, H—Ar); 10.32 (s, 1H, SO₂NH); 12.27 (s, 1H, NHAc).<br>¹³C NMR (DMSO-d6, 50 MHz): 20.86; 22.44; 108.34; 117.30; 119.38; 121.37; 126.64; 129.41; 129.62; 135.16; 136.56; 138.22; 143.19; 148.07; 157.97; 168.67. |
| JG26 | 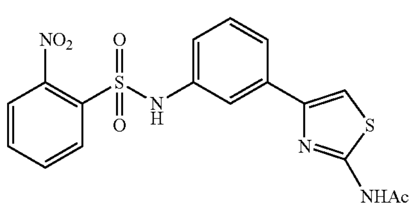 [SMILES: CC(=O)Nc1nc(-c2cccc(NS(=O)(=O)c3ccccc3[N+](=O)[O-])c2)cs1] | MS (ESI) m/z = 441 [M + Na]⁺<br>¹H NMR (DMSO-d6, 200 MHz): δ 2.16 (s, 1H, Ac); 7.07 (d, 1H, H—Ar); 7.32 (t, 1H, H—Ar); 7.52 (s, 1H, H—Ar); 7.61 (d, 1H, H—Ar); 7.71 (m, 1H, H—Ar); 7.84 (m, 2H, H—Ar); 7.98 (m, 2H, H—Ar); 10.85 (s, 1H, SO₂NH); 12.28 (s, 1H, NHAc).<br>¹³C NMR (DMSO-d6, 50 MHz): 22.45; 108.55; 118.07: 120.07; 122.19; 124.61; 129.63; 131.22; 132.49; 134.64; 135.36; 137.00; 147.83; 147.87; 158.03; 168.70. |

-continued

| Ex | Chemical structure | Spectral Data (δ in ppm) |
|---|---|---|
| JG27A | 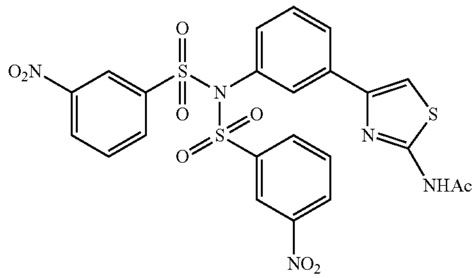 [SMILES: CC(=O)Nc1nc(-c2cccc(N(S(=O)(=O)c3cccc([N+](=O)[O-])c3)S(=O)(=O)c3cccc([N+](=O)[O-])c3)c2)cs1] | MS (ESI) m/z = 626 [M + Na]+<br>1H NMR (DMSO-d6, 200 MHz): δ 2.16 (s, 3H, Ac); 7.10 (d, 1H, H—Ar); 7.54 (t, 1H, H—Ar); 7.74 (m, 2H, H—Ar); 8.02 (t, 2H, H—Ar); 8.12 (d, 1H, H—Ar); 8.29 (d, 2H, H—Ar); 8.53 (s, 2H, H—Ar); 8.71 (d, 2H, H—Ar); 12.27 (s, 1H, NH).<br>13C NMR (DMSO-d6, 50 MHz): 22.41; 30.60; 109.55; 122.92; 127.92; 128.28; 129.55; 130.22; 130.37; 131.86; 133.26; 133.95; 135.96; 139.14; 146.59; 147.92; 158.16; 168.67. |
| JG27B | 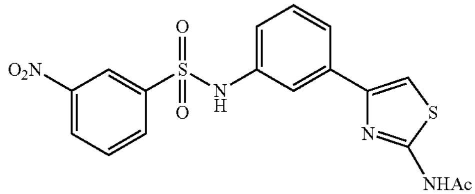 [SMILES: CC(=O)Nc1nc(-c2cccc(NS(=O)(=O)c3cccc([N+](=O)[O-])c3)c2)cs1] | MS (ESI) m/z = 441 [M + Na]+<br>1H NMR (DMSO-d6, 200 MHz): δ 2.16 (s, 3H, Ac); 7.01 (d, 1H, H—Ar); 7.29 (t, 1H, H—Ar); 7.53 (s, 1H, H—Ar); 7.60 (d, 1H, H—Ar); 7.72 (s, 1H, H—Ar); 7.85 (t, 1H, H—Ar); 8.14 (d, 1H, H—Ar); 8.44 (d, 1H, H—Ar); 8.51 (s, 1H H—Ar); 10.67 (s, 1H, SO2NH); 12.26 (s, 1H, NHAc).<br>13C NMR (DMSO-d6, 50 MHz): 22.43; 30.70; 35.71; 108.58; 118.30; 120.22; 121.32; 122.24; 127.57; 129.67; 131.33; 132.52; 135.37; 137.28; 140.83; 147.80; 157.99; 162.23; 168.67. |
| JG28A | 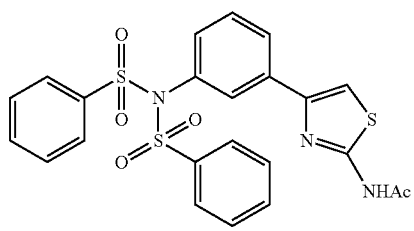 [SMILES: CC(=O)Nc1nc(-c2cccc(N(S(=O)(=O)c3ccccc3)S(=O)(=O)c3ccccc3)c2)cs1] | MS (ESI) m/z = 536 [M + Na]+<br>1H NMR (DMSO-d6, 200 MHz): δ 2.16 (s, 3H, Ac); 6.91 (d, 1H, H—Ar); 7.48 (t, 1H, H—Ar); 7.65-7.73 (m, 6H, H—Ar); 7.85 (m, 6H, H—Ar); 8.04 (d, 1H, H—Ar); 12.30 (s, 1H, NH).<br>13C NMR (DMSO-d6, 50 MHz): 22.41; 109.19; 127.34; 127.96; 128.56; 129.55; 129.81; 130.19; 133.91; 134.71; 135.55; 138.35; 146.86. 158.17; 168.68. |
| JG28D | 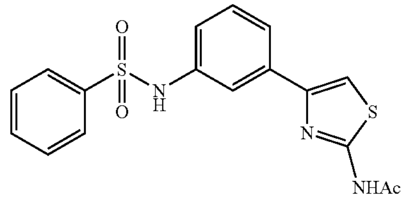 [SMILES: CC(=O)Nc1nc(-c2cccc(NS(=O)(=O)c3ccccc3)c2)cs1] | MS (ESI) m/z = 396 [M + Na]+<br>1H NMR (DMSO-d6, 200 MHz): δ 2.14 (s, 3H, Ac); 6.99 (d, 1H, H—Ar); 7.24 (t, 1H, H—Ar); 7.47-7.58 (m, 5H, H—Ar); 7.67 (t, 1H, H—Ar); 7.75 (dd, 2H, H—Ar); 10.37 (s, 1H, SO2NH); 12.25 (s, 1H, NHAc).<br>13C NMR (DMSO-d6, 50 MHz): 22.44; 108.37; 117.51; 119.60; 121.52; 126.57; 129.20; 129.42; 132.84; 135.17; 138.08; 139.39; 148.01; 157.95; 168.66 |
| JG9 | 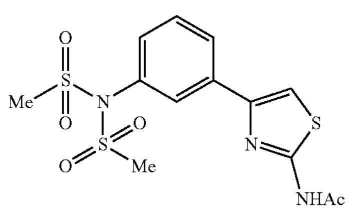 [SMILES: CC(=O)Nc1nc(-c2cccc(N(S(C)(=O)=O)S(C)(=O)=O)c2)cs1] | MS (ESI) m/z = 412 [M + Na]+<br>1H NMR (DMSO-d6, 200 MHz): δ 2.16 (s, 1H, Ac); 3.56 (s, 6H, 2SO2Me); 7.52 (m, 2H, H—Ar); 7.80 (s, 1H, H—Ar); 8.01 (m, 2H, H—Ar); 12.33 (s, 1H, NH).<br>13C NMR (DMSO-d6, 50 MHz): 24.01; 47.43; 105.01; 114.19; 116.32; 117.51; 130.04; 133.75; 147.24; 150.18; 164.23 168.92. |
| JG32 | 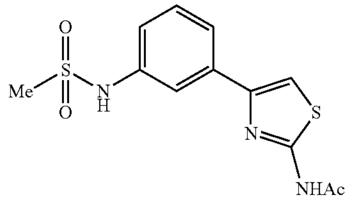 [SMILES: CC(=O)Nc1nc(-c2cccc(NS(C)(=O)=O)c2)cs1] | MS (ESI) m/z = 334 [M + Na]+<br>1H NMR (DMSO-d6, 200 MHz): δ 2.16 (s, 1H, Ac); 3.00 (s, 3H, SO2Me); 7.14 (d, 1H, H—Ar); 7.38 (t, 1H, H—Ar); 7.56 (s, 1H, H—Ar); 7.62 (d, 1H, H—Ar); 7.77 (s, 1H, H—Ar); 9.84 (s, 1H, SO2NH); 12.30 (s, 1H, NH).<br>13C NMR (DMSO-d6, 50 MHz): 22.44; 108.43; 117.05; 119.39; 121.32; 129.60; 135.39; 138.80; 148.22; 157.97; 168.69. |

| Ex | Chemical structure | Spectral Data (δ in ppm) |
|---|---|---|
| HA-15-A | 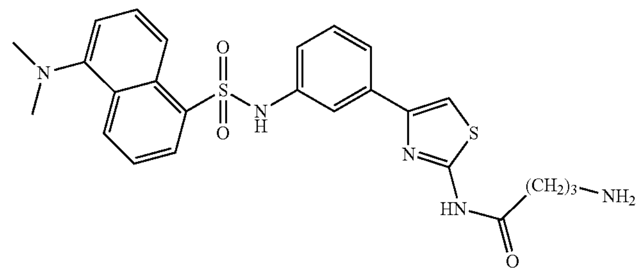 | MS (ESI) m/z = 560.2 [M + Na]+<br>¹H RMN (200 MHz, DMSO-d₆) δ: 1.42 (m, 2H), 1.69 (m, 4H), 2.48 (t, J = 7.2 Hz, 2H), 2.75 (s, 6H), 2.93 (dd, J = 14.4, 7.1 Hz, 2H), 6.88 (m, 1H), 7.05 (m, 2H), 7.19 (d, J = 7.6 Hz, 1H), 7.40 (ddd, J = 7.4, 5.3, 4.1 Hz, 2H), 7.59 (m, 2H), 8.19 (dd, J = 7.4, 1.0 Hz, 1H), 8.41 (t, J = 8.3 Hz, 2H).<br>¹³C RMN (50 MHz, DMSO-d₆) δ: 25.3; 27.2; 28.3; 42.0; 46.3; 105.1; 114.2; 120.1; 123.7; 124.8; 127.0; 128.3; 131.0; 133.0; 134.5; 139.1; 142.8; 150.3; 151.3; 165.3; 173.1. |

Example 8

Anti-Cancer Activities of Compounds of the Invention

Material & Methods
Experimental Protocol for Assessment of Potency and Efficacy
Cell Cultures Normal human melanocytes (NHM) prepared from foreskins of newborns were grown under 5% $CO_2$ at 37° C. in MCDB 153 (Sigma) supplemented with 2% FCS, bovine pituitary extract (10 µg/ml), PMA (8 nM), bFGF (ing/nil), insulin (5 µg/ml), hydrocortisone (0.5 µg/ml), forskolin (10 µM), gentamicin (20 µg/ml), penicillin/streptomycin/amphotericin B (100 U/ml) (Invitrogen).

Normal human fibroblasts prepared from foreskins of newborns were grown under 5% $CO_2$ at 37° C. in DMEM medium supplemented with 10% FCS and penicillin/streptomycin (100 U/ml/50 mg/ml).

Different melanoma cell lines were purchased from American Tissue Culture Collection (Molsheim, France). Cells were grown in RPMI 1640 (A375, WM9 and patient melanoma cells) or in DMEM medium (Me1501) supplemented with 10% FCS and penicillin/streptomycin (100 U/ml/50 mg/ml) at 37° C. and 5% $CO_2$.

Patient melanoma cells were prepared from biopsy after digestion for 1-2 h with collagenase A (0.33 U/ml), dispase (0.85 U/ml) and Dnase I (144 U/ml) at 37° C. Large debris were removed by filtration through a 70-mm cell strainer.

Trypan Blue Assays

Cells were seeded in 6-well plates (60000 cells/well), depleted and incubated with compounds for the times indicated. Then cells were detached in the presence of 2000 of HyQTase (Thermo) and 2 ml of RPMI 1640 Glutamax (Gibco) was added to the cell solution. 10 µl of this solution was stained for 1 minute with 10 µl of 0.4% trypan blue before counting with a Malassez chamber.

Western Blot Assays

Proteins were extracted in Fisher buffer containing TRIS-HCl pH 7.5 50 mM, NaCl 15 mM, Triton X-100 1% and proteases and phosphatases inhibitors. Briefly, cell lysates (30 µg) were separated by SDS-PAGE, transferred onto a PVDF membrane (Millipore, Molsheim, France) and then exposed to the appropriate antibodies. Proteins were visualized with the ECL system from Amersham (Arlington, Heights, Ill., USA). The western blots shown are representative of at least 3 independent experiments.

In Vivo Experiments

Athymic BALB/C nu/nu mice (Harlan) were used. The animals were 6 weeks old and weighed between 20 and 25 g. The mice were housed in the animal's C3M in a 12 h/12 h cycle. The animals received water and food ad libitum. Mice were first acclimated for one week and then injected with A375 cells (2.5 million cells in 200 µl of PBS) subcutaneously into the right and left sides. Treatment was started eight days after injection of cancer cells (when tumors were visible). The various compounds were diluted in a mixture of Labrafil (90%) (Gattefosse), Tween 80 (1%) and N,N-Dimethylacetamide (9%). Five groups of six mice treated every day intraperitoneally with 0.7 mg/day of PLX4032, SR44 (HA15), SR47 (HA32), SR50 (JG25) or with the mixture of Labrafil in control were defined. Three times a week the tumor size was measured using a caliper.

Results

1. HA15 Inhibits Cell Viability of Melanoma Cells and Other Types of Cancer Cells.

The effect of compound on cell viability was studied on different types of cells. As illustrated in FIG. 1, cell viability is evaluated by measuring the number of cells alive in samples of two different kind of prostate cells, respectively noted LNCAP and PC3, of breast cells noted MCF7, of colon cells noted HT29, of metastatic melanoma cell lines A375 and of melanoma cells from patients noted GIC. Cancer cells from prostate, breast, colon and melanoma A375 came from cell lines cultures. Cell cultures of melanoma cells GIC were prepared from lymph node metastasis from human patient with melanoma. To determine the effect of compound HA15 on cell viability of the studied cells, 10 µM of ciglitazone or 10 µM of HA15 were added to the cell samples. The measure of cell viability was performed by cell counting using the trypan blue exclusion method.

Results are expressed as percentage of cells alive relatively to the number of living cells in the presence of DMSO, which corresponds to the negative control associated to the 100% value. Ciglitazone is a synthetic ligand of the nuclear receptor PPAR gamma, from the thiazolidinedione family. This compound is used in the treatment of type 2 diabetes and has anti-tumor effects. In preliminary studies, it has been shown that ciglitazone led to the massive death of cells from melanomas, by apoptosis in in vitro and in vivo studies. Therefore, ciglitazone has been chosen as a positive control in the experiment illustrated in FIG. 1. Results show that, contrary to cells placed in the presence of DMSO, cells LNCAP, PC3, MCF7, HT29, A375 and GIC in the presence of ciglitazone or compound HA15 have their viability greatly reduced. As for the positive control with ciglitazone, compound HA15 inhibits cell viability of cancer cells LNCAP, PC3, MCF7, HT29, A375 and GIC.

2. HA15 does not Inhibit Cell Viability of Normal Cells.

The effect of compound HA15 on cell viability of melanocytes and fibroblasts was studied, as illustrated by FIG.

2. Primary cell cultures of human normal melanocytes were prepared from human foreskin. In order to determine the effect of compound HA15 on cell viability of melanocytes and fibroblasts, 10 μM of ciglitazone or 10 μM of HA15 were added to the cell samples. The measure of cell viability was performed in the same way as for FIG. 1 The cell viability in the presence of ciglitazone is also studied. Results show that the cell viability of normal melanocytes and fibroblasts is not affected by both compounds ciglitazone and HA15demonstrating that compound HA15 is not toxic for normal cells.

3. [HA15] and [SR50] Inhibit Tumor Development in the Mouse.

To assess a potential antineoplastic effect of [HA15] and [SR50] in vivo, A375 melanoma cells ($2.5 \times 10^6$) were injected subcutaneously in 6-week-old female athymic nude mice and treated 5 days later by injection of vehicle (labrafil) or different compounds such as PLX4032, [HA15] and [SR50] (0.7 mg/mouse/day) over a period of 24 days. PLX4032 also known as RO5185426 or vemurafenib, is a drug authorized since August 2011 for the treatment of melanoma and is used here as a positive control. Untreated control mice rapidly developed visible tumors, and dramatic tumor growth is observed throughout the course of the study. In contrast, treatment of mice with [HA15], [SR50] and PLX4032 markedly attenuated the ability of cells to develop visible tumors. Indeed, the tumor size was more than 500 mm³ 24 days after injection of labrafil against less than 100 mm³ 24 days after injection of [HA15], [SR50] and PLX4032. These data clearly demonstrate that [HA15] or [SR50] as PLX4032 has anti-melanoma activity in vivo.

4. The effect of Compounds [HA15], [HA19], [HA20], [HA21], [HA22], [HA24], [HA25], [HA26], [HA27], [HA27di], [HA29], [HA30], [HA31], [HA32], [HA33], [HA34], [HA35], [HA36], [HA37] and [HA38] on cell viability.

In order to determine the effect of the compounds on cell viability, the measure of cell viability was performed in the same way as for FIG. 1. Results are expressed as the percentage of cells alive relatively to the number of living cells in the presence of DMSO, which is a negative control, as for FIG. 1.

NS (No Stimulated) and DMSO are used as negative control. Results show that all tested compounds inhibit cell viability.

5. [HA15], [HA32] and [SR50] Inhibit Viability of Cells Resistant to Dabrafenib.

Melanoma cells resistant to dabrafenib wee prepared from patients treated and presented a resistance to dabrafenib. dabrafenib, [HA15], [SR47] and [SR50] were tested on these resistant cells, in order to determine their activity on cell viability of resistant melanoma cells, as illustrated in FIG. 5. [HA15], [HA32] and [SR50] contrary to dabrafenib inhibit cell viability of resistant melanoma cells indicating that the mechanism of action of [HA15], [HA32] and [SR50] is different from dabrafenib and hence that the compounds of the invention are good candidates for a combination treatment with dabrafenib or with other chemotherapeutical drugs, for treating melanoma.

6. Compounds [HA15], [SR44], [HA19], [HA20], [HA21], [HA22], [HA24], [HA25], [HA26], [HA27], [HA27di], [HA29], [HA29di] [HA30], [HA31], [HA32], [HA33], [HA34], [HA35], [HA36], [HA37] and [HA38] have a Mechanism of Action that is Different from and Dabrafenib on MAP Vemurafenib Activation.

To demonstrate that the mechanism of action of the compounds of the invention differs from dabrafenib phosphorylation i.e. activation of MAP vemurafenib was analyzed. Indeed, dabrafenib as PLX4032 inhibits activation of B-Raf on B-Raf V600E mutated melanoma. The inhibition of B-Raf leads to inhibition of MAP Vemurafenib cascade and could be visualized through inhibition of MAP vemurafenib phosphorylation. As presented in FIG. 6, dabrafenib led to complete inhibition of MAP vemurafenib phosphorylation in comparison to negative control (DMSO). As expected, dabrafenib did not modulate MAP vemurafenib expression. In contrast, the compounds of the invention do not modulate MAP vemurafenib phosphorylation indicating that the mechanism of action is different from dabrafenib.

REFERENCES

Throughout this application, various references describe the state of the art to which this invention pertains. The disclosures of these references are hereby incorporated by reference into the present disclosure.

The invention claimed is:

1. A method of treating cancer selected from the group consisting of melanoma, prostate cancer, breast cancer and colon cancer in a patient in need thereof, comprising
administering to said patient a therapeutically effective amount of a compound of general formula (1)

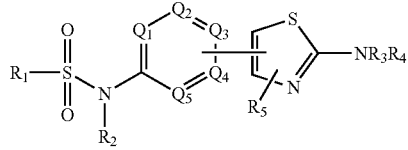

wherein
$Q_1$ to $Q_5$ are identical or different and represent $CR_6$,
$R_1$ represents phenyl or napthyl which may be substituted with from 5 to 7 substituents selected from $R_6$, halo, CN, $NO_2$, $CF_3$, $OCF_3$, $COOR_6$, $OCOR_6$, $SO_2NR_6R_7$, $CONR_6R_7$, $NR_6R_7$, $NR_6COR_7$, $(CH_2)_p$—$NR_6R_7$, $(CH_2)_p$—$OR_6$ and $(CH_2)_p SR_6$,
$R_2$ is $SO_2R_1$ or $R_6$,
$R_3$ is $R_6$ and $R_4$ is selected from $COR_8$ and $R_6$,
$R_5$ is $R_6$,
$R_6$ and $R_7$ are identical or different and represent H or alkyl,
$R_8$ is selected from H, alkyl, cycloalkyl, aryl, and alkylaryl, wherein aryl may be substituted with from one to four $R_5$ substituents which are identical or different, or $R_8$ represents —$(CH_2)_q$—$NR_6R_7$, wherein p represents an integer from 0 to 6 and q represents an integer from 0 to 6,
wherein the thiazolyl group is linked to the 6-membered group in meta or para position with respect to the sulfonamide group,
and wherein the thiazolyl group is linked to the 6-membered group in position α or β with respect to the S atom,
or a pharmaceutically acceptable salt and/or stereoisomer, tautomer, solvate or isotopic variant thereof.

2. The method of claim 1, wherein said patient is an animal or human.

3. The method of claim 1, wherein said cancer is melanoma.

* * * * *